United States Patent
Antilla et al.

(10) Patent No.: US 8,513,452 B1
(45) Date of Patent: Aug. 20, 2013

(54) BRøNSTED ACID-CATALYZED ASYMMETRIC ALLYLATION AND PROPARGYLATION OF ALDEHYDES

(75) Inventors: Jon Clarence Antilla, Tampa, FL (US); Pankaj Jain, Tampa, FL (US)

(73) Assignee: University of South Florida, Tampa, FL (US)

( * ) Notice: Subject to any disclaimer, the term of this patent is extended or adjusted under 35 U.S.C. 154(b) by 8 days.

(21) Appl. No.: 13/151,705

(22) Filed: Jun. 2, 2011

Related U.S. Application Data

(60) Provisional application No. 61/350,611, filed on Jun. 2, 2010.

(51) Int. Cl.
  C07F 9/12 (2006.01)
(52) U.S. Cl.
  USPC .............................................. 558/86; 558/73
(58) Field of Classification Search
  USPC ...................................................... 558/73, 86
  See application file for complete search history.

(56) References Cited

PUBLICATIONS

Akiyama. 2007. "Stronger Bronsted Acids." Chem. Rev. vol. 107. pp. 5744-5758.
Althaus et al. 2010. "Application of the Lithiation—Borylation Reaction to the Preparation of Enantioenriched Allylic Boron Reagents and Subsequent In Situ Conversion into 1,2,4-Trisubstituted Homoallylic Alcohols with Complete Control over All Elements of Stereochemistry." J. Am. Chem. Soc. vol. 132. pp. 4025-4028.
Barnett et al. 2009. "The Mechanism and an Improved Asymmetric Allylboration of Ketones Catalyzed by Chiral Biphenols." Agnew. Chem. Int. Ed. vol. 48. pp. 8679-8682.
Boldrini et al. "Enantioselective Synthesis of Homo-allylic Alcohols Chiral Allylic Tin(iv) (+)-Diethyl Tartrate Complexes and Aldehydes." J. Chem. Soc. Chem. Commun. pp. 685-686.
Brown et al. 1983. "Asymmetric Carbon-Carbon Bond Formation via B-Allyldiisopinocampheylborane. Simple Synthesis of Secondary Homoallylic Alcohols with Excellent Enantiomeric Purities." J. Am. Chem. Soc. vol. 105. pp. 2092-2093.
Brown et al. 1986. "Enantiomeric (Z)- and (E)-Crotyldiisopinocampheylboranes. Synthesis in High Optical Purity of All Four Possible Stereoisomers of Beta-Methylhomosllyl Alcohols." J. Am. Chem. Soc. vol. 108. pp. 293-294.
Burgos et al. 2005. "Asymmetric Allyl- and Crotylboration with the Robust, Versatile, and Recyclable 10-TMS-9-borabicyclo[3.3.2]decanes." J. Am. Chem. Soc. vol. 127. pp. 8044-8049.
Denmark et al. 2001. "Lewis Base Activation of Lewis Acids: Catalytic Enantioselective Allylation and Propargylation of Aldehydes." J. Am. Chem. Soc. vol. 123. pp. 6199-6200.
Doyle et al. 2007. "Small-Molecule H-Bond Donors in Asymmetric Catalysis." Chem. Rev. vol. 107. pp. 5713-5743.
Evans et al. 2001. "Highly Enantioselective Syntheses of Homopropargylic Alcohols and Dihydrofurans Catalyzed by a Bis(oxazolinyl)pyridine-Scandium Triflate Complex." J. Am. Chem. Soc. vol. 123. pp. 12095-12096.
Fandrick et al. 2010. "Copper Catalyzed Asymmetric Propargylation of Aldehydes." J. Am. Chem. Soc. vol. 132. pp. 7600-7601.
Francais et al. 2010. "Total Synthesis of the Anti-Apoptotic Agents Iso-and Bongkrekic Acids." Org. Lett. vol. 12. No. 2. pp. 340-343.
Furuta et al. 1991. "Chiral (Acyloxy)borane Catalyzed Asymmetric Allylation of Aldehydes." Synlett. p. 561-562.
Gonzalez et al. 2009. "Borabicyclo[3.3.3]decanes and the Steroselective Asymmetic Synthesis of 1,3-Diol Sterotriads from 1-3-Diborylpropenes." J. Am. Chem. Soc. vol. 131. pp. 1269-1273.
Hackman et al. 2004. "Highly Diastereo- and Enantioselective Reagents for Aldehyde Crotylation." Org. Lett. vol. 6. No. 23. pp. 4375-4377.
Hall. 2007. "Lewis and Bronsted Acid Catalyzed Allylboration of Carbonyl Compounds: From Discovery to Mechanism and Applications." Synlett. No. 11. pp. 1644-1655.
Hanawa et al. 2003. "Catalytic Asymmetric Allylation of Aldehydes and Related Reactions with Bis(((S)-binaphthoxy)(isopropoxy)titanium) Oxide as a Mu-Oxo-Type Chiral Lewis Acid." Chem.Eur. J. vol. 9. pp. 4405-4413.
Haruta et al. 1982. "Chiral Allenylboronic Esters: A Practical Reagent for Enantioselective Carbon-Carbon Bond Formation." J. Am. Chem. Soc. vol. 104. pp. 7667-7669.
Hoffmann et al. 1979. "Diastereoselective Synthesis of Beta-Methyl Homoallyl Alcohols." Angew. Chem., Int. Ed. Engl. vol. 18. No. 4. pp. 306.
Hoffmann et al. 1979. "On the Absolute Stereochemistry of C-2 and C-3 in Stegobinone." Tetrahedron Lett. No. 48. pp. 4653-4656.
Hoffmann et al. 1981. "Stereoselective Synthesis of Alcohols. 8. Diastereoselective Synthesis of Beta-Methylhomoallyl Alcohols via Crotylboronates." J. Org. Chem. vol. 46. pp. 1309-1314.
Hoffmann et al. 2005. "A Powerful Bronsted Acid Catalyst for the Organocatalytic Asymmetric Transfer Hydrogenation of Imines." Angew. Chem., Int. Ed. vol. 44. pp. 7424-7427.
Huang et al. 2003. "Single Enantiomers From a Chiral-Alcohol Catalyst." Nature vol. 424. pp. 146.
Ikeda et al. 1986. "Chiral Allenylboronic Esters as a Practical Reagent for Enantioselective Carbon-Carbon Bond Formation. Facile Synthesis of (−)-Ipsenol." J. Am. Chem. Soc. vol. 108. pp. 483-486.
Inoue et al. 2004. "Studies on Catalytic Asymmetric Nozaki-Hiyama Propargylation." Org. Lett. vol. 6. No. 17. pp. 2977-2980.
Iseki et al. . 1998. "Asymmetric Allenylation of Aliphatic Aldehydes Catalyzed by a Chiral Formamide." Tetrahedron: Asymmetry. vol. 9. pp. 2889-2894.

(Continued)

*Primary Examiner* — Wu-Cheng Winston Shen
*Assistant Examiner* — Karen Cheng
(74) *Attorney, Agent, or Firm* — Robert J. Varkonyi; Smith & Hopen, P.A.

(57) ABSTRACT

A method synthesizing homoallylic or homopropargylic alcohols was developed to react aldehydes with allyl boronates, such as allylboronic acid pinacol ester, or allenylborates in the presence of a catalytic amount of a chiral binaphthyl-derived chiral phosphoric acid. The method showed enhanced enantiocontrol and chemical yield, which increased with lower temperatures. A large series of aldehydes were tested under these catalytic conditions and wide successful substrate scope was found, including aryl, heteroaryl, aromatic aldehydes, heteroaryl aldehydes, α,β-unsaturated aldehydes and aliphatic aldehydes, and alkyl aldehydes. Likewise, the use of crotyl boronates (E and Z) were successfully reacted with aryl aldehydes under the conditions to allow for highly enantio- and diasteo-selective crotylation.

13 Claims, 5 Drawing Sheets

(56) References Cited

PUBLICATIONS

Ishiyama et al. 2002. "Acceleration Effect of Lewis Acid in Allylboration of Aldehydes: Catalytic, Regiospecific, Diastereospecific, and Enantioselective Synthesis of Homoallyl Alcohols." J. Am. Chem. Soc. vol. 124. pp. 12414-12415.

Jain et al. 2010. "Chiral Bronsted Acid-Catalyzed Allylboration of Aldehydes." J. Am. Chem. Soc. vol. 132. pp. 11884-11886.

Keck et al. 1993. "Catalytic Asymmetric Allylation of Aldehydes." J. Am. Chem. Soc. vol. 115. pp. 8467-8468.

Keck et al. 1994. "Asymmetric Synthesis of Homopropargylic Alcohols from Aldehydes and Allenyltri-n-butylstannane." Tetrahedron Lett. vol. 35. No. 45. pp. 8323-8324.

Corey et al. 1989. "A Practical and Efficient Method for Enantioselective Allylation and Aldehydes." J. Am. Chem. Soc. vol. 111. pp. 5495-5496.

Kennedy et al. 2002. "Dramatic Rate Enhancement with Preservation of Stereospecificity in the First Metal-Catalyzed Additions of Allylboronates." J. Am. Chem. Soc. vol. 124. pp. 11586-11587.

Kim et al. 2008. "Enantioselective Iridium-Catalyzed Carbonyl Allylation from the Alcohol or Aldehyde Oxidation Level via Transfer Hydrogenative Coupling of Allyl Acetate: Departure from Chirally Modified Allyl Metal Reagents in Carbonyl Addition." J. Am. Chem. Soc. vol. 130. pp. 14891-14899.

Kinnaird et al. 2002. "Strained Silacycles in Organic Synthesis: A New Reagent for the Enantioselective Allylation of Aldehydes." J. Am. Chem. Soc. vol. 124. pp. 7920-7921.

Kister et al. 2009. "Stereoselective Synthesis of Gamma-Substituted (z)-Allylic Boranes via Kinetically Controlled Hydroboration of Allenes with 10-TMS-9-borabicyclo[3.3.2]decane." J. Am. Chem. Soc. vol. 131. pp. 14174-14175.

Lai et al. 2005. "Nonracemic Homopropargylic Alcohols via Asymmetric Allenylboration with the Robust and Versatile 10-TMS-9-borabicyclo[3.3.2]decanes." Org. Lett. vol. 7. No. 5. pp. 709-802.

Lee et al. 2004. "Silicon-Assisted Proprargylic Transfer to Aldehydes." pp. 2456-2457.

Lee et al. 2005. "Stereochemical Diversity in Chiral Ligand Design: Discovery and Optimization of Catalysts for the Enantioselective Addition of Allylic Halides to Aldehydes." Org. Lett. vol. 7. No. 9. pp. 1837-1839.

Li et al. 1989. "Transition Structures for the Allylboration Reactions of Formaldehyde by Allylborane and Allylboronic Acid." J. Am. Chem. Soc. vol. 111. pp. 1236-1240.

Lou et al. 2006. "Asymmetric Allylboration of Ketones Catalyzed by Chiral Diols." J. Am. Chem. Soc. vol. 128. pp. 12660-12661.

Lou et al. 2007. "Asymmetric Allylboration of Acyl Imines Catalyzed by Chiral Diols." J. Am. Chem. Soc. vol. 129. pp. 15398-15404.

Malkov et al. 2002. "Chiral 2,2'-Bipyridine-Type N-Monoxides as Organocatalysts in the Enantioselective Allylation of Aldehydes with Allyltrichlorosilane." Org. Lett. vol. 4. No. 6. pp. 1047-1049.

Malkov et al. 2003. "Quinox, a Quinoline-Type N-Oxide, as Organocatalyst in the Asymmetric Allylation of Aromatic Aldehydes with Allytrichlorosilanes: The Role of Arene-Arene Interactions." Chem. Int. Ed. vol. 42. pp. 3674-3677.

McDonald et al. 1996. "Asymmetric Synthesis of Nucleosides via Molybdenum-Catalyzed Alkynol Cycloisomerization Coupled with Stereoselective Glycosylations of Deoxyfuranose Glycals and 3-Amidofuranose Glycals." J. Am. Chem. Soc. vol. 118. pp. 6648-6659.

Momiyama et al. 2009. "Chiral Phosphoric Acid-Governed Anti-Diastereoselective and Enantioselective Hetero-Diels-Alder Reaction of Glyoxylate." J. Am. Chem. Soc. vol. 131. pp. 12882-12883.

Nakashima et al. 2006. "Design of Chiral N-Triflyl Phosphoramide as a Strong Chiral Bronsted Acid and Its Application to Asymmetric Diels-Alder Reaction." J. Am. Chem. Soc. vol. 128. pp. 9626-9627.

Naodovic et al. 2008. "TBOxCr" Cl-Catalyzed Enantioselective Synthesis of 1,3-Butadien-2-ylcarbinols. Org. Lett. vol. 10. No. 18. pp. 4053-4055.

O'Sullivan et al. 2004. "A Concise Synthesis of the Octalactins." J. Am. Chem. Soc. vol. 126. pp. 2194-2207.

Panek et al. 1991. "Diastereofacial Selectivity with Optocally Active Alpha-Substituted Beta-Silyl-(E)-Hexenoates. Enantioselective Construction of Homoallylic Ethers via Reaction with Aryl Acetals." J. Am. Chem. Soc. vol. 113. pp. 6594-6600.

Ramachandran et al. 2002. "Boron-Based Reducing Agents for the Asymmetric Reduction of Functionalized Ketones and Ketimines." Aldrichimica Acta. vol. 35. No. 1. Entire book.

Bold et al. 1989. "Enantioselektive Synthase von D-threo-beta-Hydroxy-alpha-aminosauren mit Titan-Kohkenhydrat-Komplexen." M. Angew. Chem. Nol. 101. No. 4. pp. 491-493.

Chemler et al. 2000. "Recent Applications of the Allylation Reaction to the Synthesis of Natural Products." In Modern Carbonyl Chemisr.; Otera, J., Ed.; Wiley-VCH: Weinheim, Germany. pp. 403-490.

Denmark et al. 2000. "Allylation of Carbonyls: Methodology and Stereochemistry." In Modern Carbonyl Chemisry; Otera, J., Ed.; Wiley-VCH: Weinheim., Germany. Chapter 10. pp. 299-350.

Lachance et al. 2008. "Allylboration of Carbonyl Compounds." Organic Reactions. vol. 73. pp. 1-3.

Yang. 2008. "Metal Allylation Reactions." Six-Membered Transition States in Organic Synthesis. Chapter 3. pp. 97-146.

Rauniyar et al. 2006. "Catalytic Enantioselective and Catalyst-Controlled Diastereofacial-Selective Additions of Allyl- and Crotylboronates to Aldehydes Using Chiral Bronsted Acids." Angew. Chem., Int. Ed. vol. 45. pp. 2426-2428.

Rauniyar et al. 2008. "Catalytic Enantioselective Allyl- and Crotylboration of Aldehydes Using Chiral Diol*SnCl4 Complexes. Optimization, Substrate Scope and Mechanistic Investigations." J. Am. Chem. Soc. vol. 130. pp. 8481-8490.

Rauniyar et al. 2004. "Lewis Acids Catalyze the Addition of Allylboronates to Aldehydes by Electrophilic Activation of the Dioxaborolane in a Closed Transition Structure." J. Am. Chem. Soc. vol. 126. pp. 4518-4519.

Rauniyar et al. 2009. "Rationally Improved Chiral Bronsted Acid for Catalytic Enantioselective Allylboration of Aldehydes with an Expanded Reagent Scope." J. Org. Chem. vol. 74. pp. 4236-4241.

Riediker et al. 1989. "Enantioselective Allylation of Carbonyl Compounds with Titanium-Carbohydrate Complexes." Angew. Chem., Int. Ed. Engl. vol. 28. No. 4. pp. 494-495.

Roush. 1991. "Allyl Organometallics." In ComprehensiVe Organic Synthesis; Trost, B. M., Ed.; Pergamon Press: Oxford, U.K. vol. 2, p. 1.

Roush et al. 1985. "Diastereo- and Enantioselective Aldehyde Addition Reactions of 2-Allyl-1,3,2-dioxaborolane-4,5-dicarboxylic Esters, a Useful Class of Tartrate Ester Modified Allylboronates." J. Am. Chem. Soc. vol. 107. pp. 8186-8190.

Reuping et al. 2008. "Asymmetric Bronsted Acid Catalysis: Enantioselective Nucleophilic Substitutions and 1,4-Additions." Angrew. Chem., Int. Ed. vol. 47. pp. 593-596.

Rueping et al. 2007. "Chiral Bronsted Acids in the Catalytic Asymmetric Nazarov Cyclization—The First Enantioselective Organocatalytic Electrocyclic Reaction." Angew. Chem., Int. Ed. vol. 46. pp. 2097-2100.

Schmidt et al. 2003. "Catalytic Asymmetric Silane Alcoholysis: Practical Access to Chiral Silanes." J. Am. Chem. Soc. vol. 125. pp. 1190-1191.

Seebach et al. 1987. "Chiral Alkoxytitanium(IV) Complexes for Enantioselective Nucleophilic Additions to Aldehydes and as Lewis Actions in Diels-Alder Reactions." Helv. Chim. Acta. vol. 70. pp. 954-974.

Shi et al. 2010. "Identification of Modular Chiral Bisphosphines Effective for Cu(I)-Catalyzed Asymmetric Allylation and Propargylation of Ketones." J. Am. Chem. Soc. vol. 132. pp. 6638-6639.

Singh et al. 2002. "Chemoenzymatic Synthesis of Optocally Active Heterocyclic Homoallylic and Homopropargylic Alcohols." Tetrahedron Asym. vol. 13. pp. 2679-2687.

Short et al. 1989. "Asymmetric Allylboration with B-Allyl-2-(trimethylsilyl)borolane." J. Am. Chem. Soc. vol. 111. pp. 1892-1894.

Sun et al. 2009. "Enantioselective Synthesis of Fluorene Derivatives by Chiral Phosphoric Acid Catalyzed Tandem Double Friedel-Crafts Reaction." Chem. Eur. J. vol. 15. pp. 8709-8712.

Terada. 2008. "Binaphthol-Derived Phosphoric Acid as a Versatile Catalyst for Enantioselective Carbon-Carbon Bond Forming Reactions." Chem. Commun. pp. 4097-4112.

Terada et al. 2008. "Enantioselective Activation of Aldehydes by Chiral Phosphoric Acid Catalysts in an Aza-ene-type Reaction Between Glyoxylate and Enecarbamate." Angew. Chem., Int. Ed. vol. 47. pp. 4122-4125.

Trost et al. 1992. "New Strategies for the Synthesis of Vitamin D Metabolites via Pd-Catalyzed Reactions." J. Am. Chem. Soc. vol. 114. 9836-9845.

Trost et al. 2008. "Total Synthesis of Bryostatin 16 Using Atom-Economical and Chemoselective Approaches." Nature. vol. 456. pp. 485-488.

Usanov et al. 2010. "Asymmetric Nozaki-Hiyama Propargylation of Aldehydes: Enhancement of Entioselectivity by Cobalt Co-Catalysis." Angew. Chem. Int. Ed. vol. 49. pp. 8169-8172.

Wada et al. 2004. "Catalytic Enantioselective Allylboration of Ketones." J. Am. Chem. Soc. vol. 126. pp. 8910-8911.

Wadamoto et al. 2003. "BINAP/AgOTf/KF/18-Crown-6 as New Bifunctional Catalysts for Asymmetric Sakurai-Hosomi Allylation and Mukaiyama Aldol Reaction." J. Org. Chem. vol. 68. pp. 5593-5601.

Wu et al. 2004. "Asymmetric Allylboration of Aldehydes and Ketones Using 3,3'-Disubstitutedbinaphthol-Modified Boronates." Org. Lett. vol. 6. No. 16. pp. 2701-2704.

Xia et al. 2006. "Catalytic Enantioselective Nozaki-Hiyama Allylation Reaction with Tethered Bis(8-quinolinolato)(TBOx)Chromium Complex." J. Am. Chem. Soc. vol. 128. pp. 2554-2555.

Yamamoto. 1991. "Propargyl and Allenyl Organametallics." Comprehensive Organic Synthesis. C. H. Heathcock, Pergamon, Oxford. vol. 2, pp. 81-98.

Yamamoto et al. 1993. "Selective Reactions Using Allylic Metals." Chem. Rev. vol. 93. pp. 2207-2293.

Minowa et al. 1987. "Asymmetric Allylation with a New Chiral Allylating Prepared From Tin(II) Triflate, Chiral Diamine, and Allylaluminum." Bull. Chem. Soc. Jpn. vol. 60. pp. 3697-3704

Yu et al. 1997. "Catalytic Asymmetric Prop-2-ynylation Involving the Use of the Bifunctional Synergetic Reagent Et2BSPri." Chem. Commun. pp. 763-764.

Yu et al. 1998. "Catalytic Asymmetric Allenylation: Regulation of the Equilibrium Between Propargyl- and Allenylstannanes During the Catalytic Process." Angew. Chem. Int. Ed. vol. 37. No. 17. pp. 2392-2395.

Yu et al. 2005. "Bronsted Acid-Catalyzed Allylboration: Short and Stereodivergent Synthesis of All Four Eupomatilone Diastereomers with Crystallographic Assignments." J. Am. Chem. Soc. vol. 127. pp. 12808-12809.

Loh et al. 1999. "A Highly Enantioselective Indium-Mediated Allylation Reaction of Aldehydes." Org. Lett. vol. 1. No. 11. pp. 1855-1857.

Denmark et al. 2003. "Catalytic Enantioselective Addition of Allytic Organometallic Reagents to Aldehydes and Ketones." Chem. Rev. vol. 103. pp. 2763-2793.

Corey et al. 1990. "A Practical and General Enantioselective Synthesis of Chiral Propa-1,2-Dienyl and Propargyl Carbinols." J. Am. Chem. Soc. vol. 112. pp. 878-879.

Costa et al. 1993. "Catalytic Asymmetric Synthesis of Homoallylic Alcohols." J. Am. Chem. Soc. vol. 115. pp. 7001-7002.

Denmark et al. 2001. "Catalytic, Enantioselective Addition of Substituted Allylic Trichlorosilanes Using a Rationally-Designed 2,2'-Bispyrrolidine-Based Bisphosphoramide." J. Am. Chem. Soc. vol. 123. pp. 9488-9489.

Chen et al. 2009. "Enantioselective Synthesis of 2-Methyl-1,2-syn- and 2-Methyl-1,2-anti-3-butenediols via Allene Hydroboration—Aldehyde Allylboration Reaction Sequences." J. Am. Chem. Soc. vol. 131. pp. 14602-14603.

Ishihara, K., Nakashima, D., Hiraiwa, Y., Yamamoto, H., The Crystallographic Structure of a Lewis Acid-Assisted Chiral Bronsted Acid as an Enantioselective Protonation Reagent for Silyl Enol Ethers. J. Am. Chem. Soc., vol. 125, No. 1 (2003), pp. 24-25.

Sigma-Aldrich, (R)-3,3'-Bis(2,4,6-triisopropylphenyl)-1,1'-binaphthyl-2,2'-diyl hydrogenphosphate. USA Home. Accessed on Jan. 11, 2013.

4h R= (2,4,6-i-Pr)-C₆H₂

4g

4a R= SiPh₃
4b R= 4-(β-Naph)-C₆H₄
4c R= 9-anthryl
4d R= Ph
4e R= (2,4,6-i-Pr)-C₆H₂
4f R= (2,4,6-CH₃)-C₆H₂

PA7: R = (2,4,6-i-Pr)-C₆H₂

PA1: R = SiPh₃
PA2: R = 4-(b-Naph)-C₆H₄
PA3: R = 9-anthryl
PA4: R = 4-(a-Naph)-C₆H₄
PA5: R = (2,4,6-i-Pr)-C₆H₂
PA5: R = (2,5-CF₃)-C₃H₃

BRØNSTED ACID-CATALYZED ASYMMETRIC ALLYLATION AND PROPARGYLATION OF ALDEHYDES

CROSS REFERENCE TO RELATED APPLICATION

This application claims priority to U.S. Provisional Patent Application 61/350,611, entitled, "Bronsted Acid-Catalyzed Asymmetric Allylation of Aldehydes", filed Jun. 2, 2010, the entire contents of which are hereby incorporated by reference.

GOVERNMENT SUPPORT

This invention was made with government support under Grant No. NIH GM-082935, awarded by the National Institutes of Health and Grant No. NSF-0847108, awarded by the National Science Foundation CAREER Program. The government has certain rights in the invention.

FIELD OF THE INVENTION

This invention relates to the synthesis of homoallyl alcohols. Specifically, the invention relates to the reaction of aldehydes with allyl boronates in the presence of a catalytic amount of a chiral phosphoric acid to produce chiral allylic alcohols with high enantiocontrol and chemical yield.

BACKGROUND OF THE INVENTION

Asymmetric allylboration of aldehydes has been an invaluable tool for the formation of carbon-carbon bonds with control over relative and absolute stereochemistry (Lachance, H.; Hall, D. G. *Org. React.* 2008, 73, 1; Denmark, S. E.; Fu, J. *Chem. ReV.* 2003, 103, 2763; Denmark, S. E.; Almstead, N. G. In *Modern Carbonyl Chemistry*; Otera, J., Ed.; Wiley-VCH: Weinheim, Germany, 2000; Chapter 10, p 299; Chemler, S. R.; Roush, W. R. In *Modern Carbonyl Chemistry*; Otera, J., Ed.; Wiley-VCH: Weinheim, Germany, 2000; p 403; Yamamoto, Y.; Asao, N. *Chem. ReV.* 1993, 93, 2207; Roush, W. R. In *Comprehensive Organic Synthesis*; Trost, B. M., Ed.; Pergamon Press: Oxford, U.K., 1991; Vol. 2, p 1). The foundation of this reaction was provided by Hoffmann's recognition of the diastereospecificity of the reaction when both (E)- and (Z)-crotylboronates are used (Hoffmann, R. W.; Ladner, W. *Tetrahedron Lett.* 1979, 20, 4653; Hoffmann, R. W.; Zeiss, H. J. *Angew. Chem., Int. Ed. Engl.* 1979, 18, 306; Hoffmann, R. W.; Zeiss, H. J. *J. Org. Chem.* 1981, 46, 1309) and Brown's highly stereoselective allylborations using pinene-derived chiral reagents (Brown, H. C.; Jadhav, P. K. *J. Am. Chem. Soc.* 1983, 105, 2092.; Brown, H. C.; Bhat, K. S. *J. Am. Chem. Soc.* 1986, 108, 293. (f) Ramachandran, P. V. *Aldrichimica Acta* 2002, 35, 23). Over the past three decades, additional methodologies that have relied upon stoichiometric chiral reagents or mediators have included work by Roush (Roush, W. R.; Walts, A. E.; Hoong, L. K. *J. Am. Chem. Soc.* 1985, 107, 8186; Chen, M.; Handa, M.; Roush, W. R. *J. Am. Chem. Soc.* 2009, 131, 14602; Kister, J.; DeBaillie, A. C.; Lira, R.; Roush, W. R. *J. Am. Chem. Soc.* 2009, 131, 14175), Masamune (Short, R. P.; Masamune, S. *J. Am. Chem. Soc.* 1989, 111, 1892), Corey (Corey, E. J.; Yu, C. M.; Kim, S. S. *J. Am. Chem. Soc.* 1989, 111, 5495), Seebach (Seebach, D.; Beck, A. K.; Imwinkelzied, R.; Roggo, S.; Wonnacott, A. *Helv. Chim. Acta* 1987, 70, 954), Duthaler (Riediker, M.; Duthaler, R. O. *Angew. Chem., Int. Ed. Engl.* 1989, 28, 494), Panek (Panek, J. S.; Yang, M. *J. Am. Chem. Soc.* 1991, 113, 6594), Leighton (Kinnaird, I. W. A.; Ng, P. Y.; Kubota, K.; Wang, X.; Leighton, J. L. *J. Am. Chem. Soc.* 2002, 124, 7920; Hackman, B. M.; Lombardi, P. J.; Leighton, J. L. *Org. Lett.* 2004, 6, 4375.), Chong (Wu, T. R.; Shen, L.; Chong, J. M. *Org. Lett.* 2004, 6, 2701), Soderquist (Burgos, C. H.; Canales, E.; Matos, K.; Soderquist, J. A. *J. Am. Chem. Soc.* 2005, 127, 8044. (m) Gonzalez, A. Z.; Roman, I. G.; Alicea, E.; Canales, E.; Soderquist, J. A. *J. Am. Chem. Soc.* 2009, 131, 1269), and Aggarwal (Althaus, M.; Mahmood, A.; Suarez, J. R.; Thomas, S. P.; Aggarwal, V. K. *J. Am. Chem. Soc.* 2010, 132, 4025).

Catalytic methods that avoid the use of stoichiometric chiral reagents have also emerged, and include work by Yamamoto (Furuta, K.; Mouri, M.; Yamamoto, H. *Synlett* 1991, 561), Umani-Ronchi (Costa, A. L.; Piazza, M. G.; Tagliavini, E.; Trombini, C.; Umani-Ronchi, A. *J. Am. Chem. Soc.* 1993, 115, 7001), Keck (Keck, G. E.; Tarbet, K. H.; Geraci, L. S. *J. Am. Chem. Soc.* 1993, 115, 8467), Denmark (Denmark, S. E.; Fu, J. *Chem. ReV.* 2003, 103, 2763; Denmark, S. E.; Fu, J. *J. Am. Chem. Soc.* 2001, 123, 9488) and others (Malkov, A.; Orsini, M.; Pernazza, D.; Muir, K. W.; Langer, V.; Meghani, P.; Kocovsky, P. *Org. Lett.* 2002, 4, 1047; Kim, I. S.; Ngai, M.; Krische, M. J. *J. Am. Chem. Soc.* 2008, 130, 14891). Also, recent catalytic allylborations by Hall (Kennedy, J. W. J.; Hall, D. G. *J. Am. Chem. Soc.* 2002, 124, 11586; Rauniyar, V.; Hall, D. G. *J. Am. Chem. Soc.* 2004, 126, 4518; Yu, S. H.; Ferguson, M. J.; McDonald, R.; Hall, D. G. *J. Am. Chem. Soc.* 2005, 127, 12808; Rauniyar, V.; Hall, D. G. *Angew. Chem., Int. Ed.* 2006, 45, 2426; Hall, D. G. *Synlett* 2007, 1644; Rauniyar, V.; Zhai, H.; Hall, D. G. *J. Am. Chem. Soc.* 2008, 130, 8481; Rauniyar, V.; Hall, D. G. *J. Org. Chem.* 2009, 74, 4236), Miyaura (Ishiyama, T.; Ahiko, T.-A.; Miyaura, N. *J. Am. Chem. Soc.* 2002, 124, 12414), Shibasaki (Wada, R.; Oisaki, K.; Kanai, M.; Shibasaki, M. *J. Am. Chem. Soc.* 2004, 126, 8910), and Schaus (Lou, S.; Moquist, P. N.; Schaus, S. E. *J. Am. Chem. Soc.* 2006, 128, 12660; Barnett, D. S.; Moquist, P. N.; Schaus, S. E. *Angew. Chem., Int. Ed.* 2009, 48, 8679) have opened new doors for the synthesis of homoallylic alcohols. Most of the current methods for enantioselective propargylations involve the use of chiral reagents (Ikeda, N.; Arai, I.; Yamamoto, H. *J. Am. Chem. Soc.* 1986, 108, 483-486; Haruta, R.; Ishiguro, M.; Ikeda, N.; Yamamoto, H. *J. Am. Chem. Soc.* 1982, 104, 7667-7669; Corey, E. J.; Yu, C.-M.; Lee, D.-H. *J. Am. Chem. Soc.* 1990, 112, 878-879; Lee, K.-C.; Lin, M,-J.; Loh, T.-P. *Chem. Commun.* 2004, 2456-2457; Lai, C.; Soderquist, J. A. *Org. Lett.* 2005, 7, 799-802). Alternatives to propargylation involving stoichiometric chiral reagents have also been developed and are limited to use of allenylic or propargylic metal reagents or intermediates (Denmark, S. E.; Fu, J. *Chem. Rev.* 2003, 103, 2763; Boldrini, G. P.; Tagliavini, E.; Trombini, C.; Umani-Ronchi, A. *J. Chem. Soc., Chem. Commun.* 1986, 685-686; Minowa, N.; Mukaiyama, T. *Bull. Chem. Soc. Jpn.* 1987, 60, 3697-3704; Keck, G. E.; Krishnamurthy, D.; Chen, X. *Tetrahedron Lett.* 1994, 35, 8323-8324; Yu, C.-M.; Yoon, S.-K.; Choi, H.-S.; Baek, K. *Chem. Commun.* 1997, 763-764; Yu, C.-M.; Yoon, S.-K.; Baek, K.; Lee, J.-Y. *Angew. Chem. Int. Ed.* 1998, 37, 2392-2395; Iseki, K.; Kuroki, Y.; Kobayashi, Y. *Tetrahedron: Asymmetry,* 1998, 9, 2889-2894; Denmark, S. E.; Wynn, T. *J. Am. Chem. Soc.* 2001, 123, 6199-6200; Evans, D. A.; Sweeney, Z. K.; Rovis, T.; Tedrow, J. S. *J. Am. Chem. Soc.* 2001, 123, 12095-12096; Hanawa, H.; Uraguchi, D.; Konishi, S.; Hashimoto, T.; Maruoka, K. *Chem.-Eur. J.* 2003, 9, 4405-4413; Inoue, M.; Nakada, M. *Org. Lett.* 2004, 6, 2977-2980; Naodovic, M.; Xia, G.; Yamamoto, H. *Org. Lett.* 2008, 10, 4053-4055; Fandrick, D. R.; Fandrick, K. R.; Reeves, J. T.; Tan, Z.; Tang, W.; Capacci, A. G.; Rodriguez, S.; Song, J.

J.; Lee, H.; Lee, H.; Yee, N. K.; Senanayake, C. H. *J. Am. Chem. Soc.* 2010, 132, 7600-7601; Usanov, D. L.; Yamamoto, H. *Angew. Chem. Int. Ed.* 2010, 49, 8169-8172; Shi, S.-L.; Xu L.-W.; Oisaki, K.; Shibasaki, M. *J. Am. Chem. Soc.* 2010, 132, 6638-6639).

Enantiomerically pure homopropargylic alcohols are highly useful intermediates and have shown a broad synthetic utility. The terminal alkyne functionality serves as a synthetic handle for coupling reactions, metathesis and heterocycle synthesis (Trost, B. M.; Dumas, J.; VIIIa, M. *J. Am. Chem. Soc.* 1992, 114, 9836-9845; McDonald, F. E.; Gleason, M. M. *J. Am. Chem. Soc.* 1996, 118, 6648; Schmidt, D. R.; O'Malley, S. J.; Leighton, J. L. *J. Am. Chem. Soc.* 2003, 125, 1190-1191; O'Sullivan, P. T.; Buhr, W.; Fuhry, M. A. M.; Harrison, J. R.; Davies, J. E.; Feeder, N.; Marshall, D. R.; Burton, J. W.; Holmes, A. B. *J. Am. Chem. Soc.* 2004, 126, 2194-2207; Trost, B. M.; Dong, G. *Nature,* 2008, 456, 485-488; Francais, A.; Leyva, A.; Etxebarria-Jardi, G. Ley, S. V. *Org. Lett.* 2010, 12, 340-343). The addition of allenic or propargylic reagents to carbonyl compounds is mechanistically similar to the corresponding reaction with the allylic reagents. However, though many useful and innovative methods exist for the synthesis of homoallylic alcohols (Denmark, S. E.; Fu, *J. Chem. Rev.* 2003, 103, 2763; Brown, H. C.; Jadhav, P. K. *J. Am. Chem. Soc.* 1983, 105, 2092; Corey, E. J.; Yu, C. M.; Kim, S. S. *J. Am. Chem. Soc.* 1989, 111, 5495; Keck, G. E.; Tarbet, K. H.; Geraci, L. S. *J. Am. Chem. Soc.* 1993, 115, 8461; Burgos, C. H.; Canales, E.; Matos, K.; Soderquist, J. A. *J. Am. Chem. Soc.* 2005, 127, 8044.; Lachance, H.; Hall, D. G. *Org. React.* 2008, 73, 1; Chen, M.; Handa, M.; Roush, W. R. *J. Am. Chem. Soc.* 2009, 131, 14602; Althaus, M.; Mahmood, A.; Suarez, J. R.; Thomas, S. P.; Aggarwal, V. K. *J. Am. Chem. Soc.* 2010, 132, 4025), the enantioselective synthesis of homopropargylic alcohols still remains a challenge. There are two main issues: the lower reactivity of the allenylic and propargylic substrates in comparison to allylic reagents, and the difficulties associated with controlling the regioselectivity (H. Yamamoto, in *Comprehensive Organic Synthesis: Propargyl and Allenyl Organometallics,* ed. C. H. Heathcock, Pergamon, Oxford, 1991, vol. 2, pp. 81-98).

However, most stereoselective methods are limited by one or more drawbacks. These include the use of stoichiometric chiral inductors, allylation reagents that are difficult to prepare or are air/moisture-sensitive, the use of undesirable metal-based catalysts such as tin, or substrates leading to toxic byproducts. Therefore, what is needed is a competent, catalytic, and practical solution for the direct enantioselective synthesis of homoallylic alcohols, an important class of versatile intermediates used in the synthesis of pharmaceuticals and natural products.

SUMMARY OF THE INVENTION

Recent developments in Brønsted acid catalyzed allylborations of aldehydes, ketones and imines has fascinated synthetic chemists (Yu, S. H.; Ferguson, M. J.; McDonald, R.; Hall, D. G. *J. Am. Chem. Soc.* 2005, 127, 12808-12809; Rauniyar, V.; Hall, D. G. *Angew. Chem., Int. Ed.* 2006, 45, 2426; Rauniyar, V.; Zhai, H.; Hall, D. G. *J. Am. Chem. Soc.* 2008, 130, 8481; Lou, S.; Moquist, P. N.; Schaus, S. E. *J. Am. Chem. Soc.* 2006, 128, 12660; Lou, S.; Moquist, P. N.; Schaus, S. E. *J. Am. Chem. Soc.* 2007, 129, 15398-15404; Barnett, D. S.; Moquist, P. N.; Schaus, S. E. *Angew. Chem., Int. Ed.* 2009, 48, 8679; Jain, P.; Antilla. J. C. *J. Am. Chem. Soc.* 2010, 132, 11884-11886), however, to there are no reports concerning the effects of a Brønsted acid on allenylboration of these compounds.

A method of synthesizing homoallyl alcohols or homopropargyl alcohols is described whereby aldehydes can be reacted with allyl boronates, such as allylboronic acid pinacol ester or allenylboronates, in the presence of a catalytic amount of a chiral phosphoric acid to produce chiral allylic or propargylic alcohols with extremely high enantiocontrol and chemical yield. The method was optimized in terms of the chiral Brønsted acid, having the formula

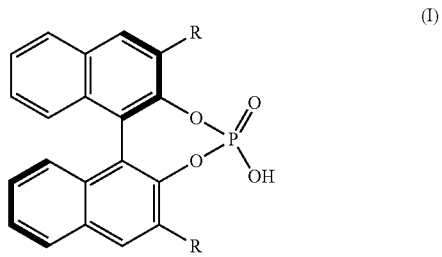

where R=SiPh3, 4-(b-Nath)-Ph, 9-anthryl, 4-a-Naph)-Ph, (2,4,6-i-Pr)-Ph, or (2,5-CF3)-Ph. Ideally, the catalyst is a a triisopropylphenyl substituted BINOL based phosphoric acid, such as (R)-TRIP-PA. The catalyst is optionally added at about 5 mol %, and about 1 mol %, including 5 mol %, 2.5 mol %, or 1 mol %. A large series of aldehydes were tested under these catalytic conditions and wide successful substrate scope was found, including aryl, heteroaryl, aromatic aldehydes, heteroaryl aldehydes, α,β-unsaturated aldehydes and aliphatic aldehydes, and alkyl aldehydes. Likewise, the use of crotyl boronates (E and Z) were successfully reacted with aryl aldehydes under the conditions to allow for highly enantio- and diasteo-selective crotylation. The reaction optionally is performed in a solvent, such as toluene, m-xylene, benzene, methylene chloride, ether, or DCM.

Further testing of the reactions showed that lowering the temperature of the reactants to between about 0° C. and about −30° C., including 0° C., −5° C., −10° C., −15° C., −20° C., −25° C., or −30° C., improved enantioselectivity. Likewise, optionally adding 4 ÅMS with at least 20 mol % improved enantioselectivity.

The discovery and development of new catalytic methods for efficient synthesis of chiral homoallylic and homopropargylic alcohols will enhance the use of these versatile intermediates in natural product synthesis.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
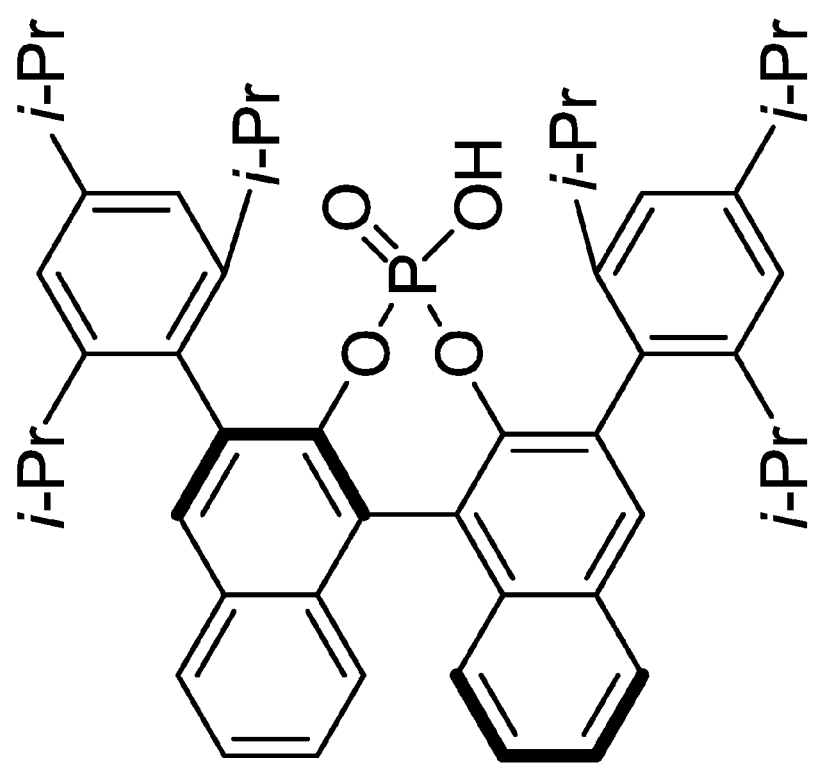
FIG. 1 is an image of the chemical structure of (R) TRIP-PA.

Binaphthyl-derived chiral phosphoric acids (PAs) have been shown to be versatile and efficient catalysts that promote a variety of enantioselective transformations. Chiral PA catalysts have found success in a large number of carbon-carbon and carbon-heteroatom bond-forming processes as well as a variety of oxidation and reduction reactions (Akiyama, T. *Chem. Rev.* 2007, 107, 5744; Doyle, A. G.; Jacobsen, E. N. *Chem. ReV.* 2007, 107, 5173; Terada, M. *Chem. Commun.* 2008, 4097). The present invention uses a new catalytic enantioselective allylation and crotylation of aldehydes with a non-metal based catalyst and is an easy to use asymmetric allylation. The allylation and crotylation uses commercially available allyl and crotyl pinacol boronate esters in a controlled, stereoselective manner utilizing an organocatalyst. Although chiral PA-catalyzed reactions involving aldehydes are very rare, (Terada, M.; Soga, K.; Momiyama, N. *Angew. Chem., Int. Ed.* 2008, 47, 4122; Momiyama, N.; Tabuse, H.; Terada, M. *J. Am. Chem. Soc.* 2009, 131, 12882.; Sun, F.-L.; Zeng, M.; Gu, Q.; You, S.-L. *Chems. Eur. J.* 2009, 15, 8709; Huang, Y.; Unni, A. K.; Thadani, A. N.; Rawal, V. H. *Nature* 2003, 424, 146; Nakashima, D.; Yamamoto, H. *J. Am. Chem. Soc.* 2006, 128, 9626; Rueping, M.; Nachtsheim, B. J.; Moreth, S. A.; Bolte, M. *Angew. Chem., Int. Ed* 2008, 47, 593. (d) Rueping, M.; Ieawsuwan, W.; Antonchick, A. P.; Nachtsheim, B. J. *Angew. Chem., Int. Ed.* 2007, 46, 2097) the enantioselective synthesis of homoallylic alcohols was investigated by reacting aldehydes with allylboronic acid pinacol ester 2 using chiral acid-catalyzed conditions. Boronate 2 is a relatively stable, nontoxic, commercially available reagent, so it was an ideal choice for our evaluation of the chemistry. The substrate scope on the aldehyde is vast thus allowing for aryl, heteroaryl, alkyl and α,β-unsaturated aldehydes.

Unless otherwise noted, the terms used herein are to be understood according to conventional usage by those of ordinary skill in the relevant art. It is to be understood that as used in the specification and in the claims, "a" or "an" can mean one or more, depending upon the context in which it is used. Thus, for example, reference to "a solvent" can mean that at least one solvent can be used.

As used herein, "about" means approximately or nearly and in the context of a numerical value or set forth means±15% of the numerical.

In the following detailed description of the preferred embodiments, reference is made to the accompanying drawings, which form a part hereof, and within which are shown by way of illustration specific embodiments by which the invention may be practiced. It is to be understood that there are other embodiments by which the invention may be practiced. It is to be understood that other embodiments may be utilized and structural changes may be made without departing from the scope of the invention.

Allylboration of Aldehydes

A screw-cap reaction tube with a stir bar was evacuated, flame-dried, and back-filled with argon. To this tube was added the (R)-TRIP-PA catalyst 4 (3.77 mg, 0.005 mmol 5 mol %), freshly distilled aldehyde (0.1 mmol, 10.1 µL), such as benzaldehyde, and 1.5 ml of dry toluene. The reaction mixture was then cooled to −30° C. followed by the addition of allylboronic acid pinacol ester 2 (23.1 µL, 0.123 mmol), dropwise over 30 seconds. The mixture was stirred overnight at this temperature under argon and then directly loaded on silica gel column, the product was separated by flash chromatography using ethyl acetate and hexanes (1:9). The product was obtained as colorless oil in 99% yield and 98% enantiomeric excess (ee) as judged by separation using a chiral HPLC (Chiralcel OD-H column using hexanes: i-PrOH=99:1).

Merck TLC plates (silica gel 60 $F_{254}$) were run under the following conditions: Ethyl acetate:Hexanes (1:4). Visualization was accomplished UV light (256 nm), with the combination of ceric ammonium molybdate as indicator. Flash column chromatography was performed with Merck silica gel (230-400 mesh). Enantiomeric excess (ee) was determined using a Varian Prostar HPLC with a 210 binary pump and a 335 diode array detector. Optical rotations were performed on a Rudolph Research Analytical Autopol IV polarimeter (λ 589) using a 700-µL cell with a path length of 1-dm. $^1$HNMR and $^{13}$C NMR were recorded on a Varian Inova-400 spectrometer with chemical shifts reported relative to tetramethylsilane (TMS). All the compounds were known compounds and were characterized by comparing their $^1$H NMR and $^{13}$C NMR values to the reported values.

During the initial investigations leading to a catalytic reaction between benzaldehyde and 2, (R)-TRIP-PA (4), seen in FIG. 1, was found to be a very effective promoter (Hoffmann, S.; Seayad, A.; List, B. *Angew. Chem., Int. Ed.* 2005, 44, 7424). Both isomers of this catalyst (R and S) are commercially available and easily prepared from BINOL (Hoffmann, S.; Seayad, A.; List, B. *Angew. Chem., Int. Ed.* 2005, 44, 7424). Upon solvent screening, toluene, m-xylene, benzene, and methylene chloride were found effective for the asymmetric synthesis of alcohol 3a, as seen in Table 1. It was determined that toluene was the most suitable solvent, allowing for a 93% ee of 3a at room temperature in a reaction time of 1 h (entry 8). The enantioselectivity was further improved by reducing the temperature to 0° C. (96% ee; entry 9) and −30° C. (98% ee; entry 10) in the presence of 5 mol % catalyst. Unexpectedly, lowering the catalyst loading to 2.5 mol % allowed for a 97% ee (entry 11), and further lowering to 1 mol % (entry 12) still allowed for an impressive 95% enantioselectivity.

TABLE 1

Optimization of the Catalytic Allylboration of Aldehydes[a]

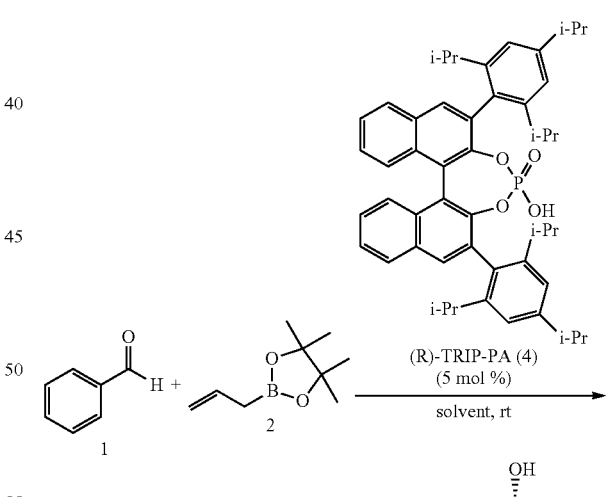

| entry | solvent | time (h) | yield (%)[b] | ee (%)[c] |
|---|---|---|---|---|
| 1 | ether | 16 | 99 | 35 |
| 2 | DCM | 16 | 99 | 88 |
| 3 | THF | 48 | 51 | 6 |
| 4 | m-xylene | 48 | 99 | 89 |
| 5 | EtOAc | 24 | 76 | 29 |
| 6 | CH2CN | 48 | 55 | 33 |
| 7 | benzamine | 2 | 99 | 92 |

TABLE 1-continued

Optimization of the Catalytic Allylboration of Aldehydes[a]

[Scheme showing benzaldehyde 1 + allyl pinacol boronate 2 with (R)-TRIP-PA (4) (5 mol %) in solvent, rt, giving homoallylic alcohol 3a]

| entry | solvent | time (h) | yield (%)[b] | ee (%)[c] |
|---|---|---|---|---|
| 8 | toluene | 1 | 99 | 93 |
| 9 | toluene[d] | 4 | 99 | 96 |
| 10 | toluene[e] | 16 | 99 | 98 |
| 11 | toluene[e,f] | 16 | 99 | 97 |
| 12 | toluene[e,g] | 16 | 99 | 95 |

[a]Reaction conditions: 1 (0.10 mmol), 2 (0.12 mmol), 5 mol % (R)-TRIP-PA, unless otherwise specified.
[b]Isolated yield.
[c]Determined by chiral HPLC analysis.
[d]Reaction conducted at 0° C.
[e]Reaction conducted at −30° C.
[f]Using 2.5 mol % catalyst.
[g]Using 1 mol % catalyst.

The optimized reaction conditions were effective in promoting the asymmetric allylboration of a wide range of aldehydes, allowing for an extremely efficient reaction, seen in Table 2. The substrate scope extended to electron-rich and electron-poor aromatic aldehydes (entries 1-11). An ester functional group was tolerated in the chemistry (entry 8), and several hindered aldehydes also were effectively allylated (entries 7, 9, and 10). Unexpectedly, heteroaryl (entry 12), α,β-unsaturated (entries 13 and 14), and aliphatic (entries 15 and 16) aldehydes were found to be allylated efficiently with high enantioselectivity. The only limits were a lowering of enantioselectivity in the reaction with some of the aliphatic aldehyde substrates, (entries 17 and 18).

TABLE 2

Asymmetric Allylboration of Aldehydes[a]

[Scheme: R-CHO (1) + allyl pinacol boronate (2), (R)-TRIP-PA (4) (% mol %), toluene, −30° C., giving 3a-r]

| entry | R | product | yield (%)[b] | ee (%)[c] |
|---|---|---|---|---|
| 1 | Ph | 3a | 99 | 98[d] |
| 2 | 4-ClC$_6$H$_4$ | 3b | 98 | 99 |
| 3 | 4-BrC$_6$H$_4$ | 3c | 99 | 99 |
| 4 | 4-NO$_2$C$_6$H$_4$ | 3d | 98 | 98 |
| 5 | 4-MeOC$_6$H$_4$ | 3e | 95 | 98 |
| 6 | 3-MeOC$_6$H$_4$ | 3f | 96 | 97 |
| 7 | 2-MeC$_6$H$_4$ | 3g | 97 | 93 |
| 8 | 4-CO$_2$MeC$_6$H$_4$ | 3h | 96 | 96 |
| 9 | 1-napththyl | 3i | 93 | 98 |
| 10 | 9-anthryl | 3j | 94 | 91 |
| 11 | piperonyl | 3k | 98 | 98 |
| 12 | 2-thienyl | 3l | 91 | 96[e] |
| 13 | Ph-CH=CH- (trans-cinnamyl) | 3m | 94 | 96 |
| 14 | Ph-C(CH$_3$)=CH- | 3n | 93 | 93 |
| 15 | Bn | 3o | 98 | 90 |
| 16 | PhCH$_2$CH$_2$ | 3p | 96 | 87[e] |
| 17 | BnOCH$_2$ | 3q | 92 | 79[e] |
| 18 | c-C$_6$H$_{11}$ | 3r | 98 | 73 |

[a]Reaction conditions: 1 (0.10 mmol), 2 (0.12 mmol), 5 mol % (R)-TRIP-PA.
[b]Isolated yield.
[c]The products were determined to be R by chiral HPLC analysis and optical rotation data in the literature.
[d]With (S)-TRIP-PA the opposite (S) enantiomer of 3a was also obtained in 98% yield and 97% ee under otherwise identical conditions.
[e]In three cases, the opposite (S) enantiomer was produced in excess using the (R)-TRIP-PA catalyst.

These examples represent a novel situation where a chiral Brønsted acid activates allylboronate esters, in the absence of a Lewis acid, in a highly enantioselective catalytic process (Yu, S. H.; Ferguson, M. J.; McDonald, R.; Hall, D. G. *J. Am. Chem. Soc.* 2005, 127, 12808. (d) Rauniyar, V.; Hall, D. G. *Angew. Chem., Int. Ed.* 2006, 45, 2426. (e) Hall, D. G. *Synlett* 2007, 1644. (f) Rauniyar, V.; Zhai, H.; Hall, D. G. *J. Am. Chem. Soc.* 2008, 130, 8481. (g) Rauniyar, V.; Hall, D. G. *J. Org. Chem.* 2009, 74, 4236).

Crotylboration of Aldehydes

Figure 2:
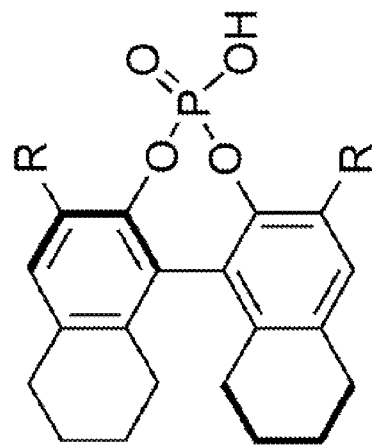
FIG. 2 is a structural diagram of catalysts evaluated for the allylboration of compounds in Table 3.
Figure 2:
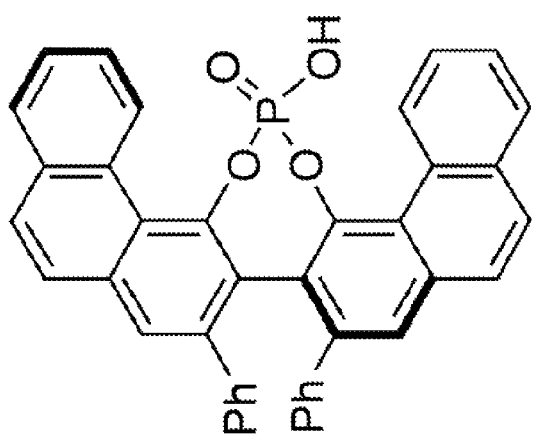
Figure 2:
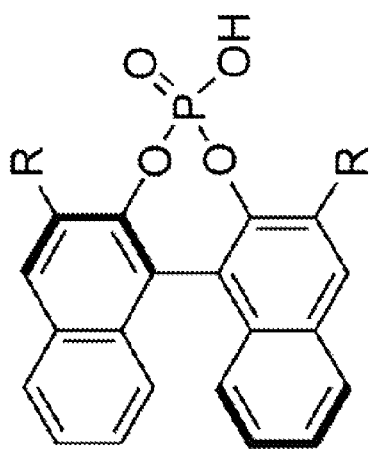

A screw-cap reaction tube with a stir bar was evacuated, flame-dried, and back-filled with argon. To this tube was added different catalysts, seen in FIG. 2, freshly distilled benzaldehyde (0.10 mmol) and 1.5 ml of dry toluene, shown in Table 3. The reaction mixture was then cooled to required temperature followed by the addition of crotyl boronic acid pinacol ester 5 (0.12 mmol), dropwise over 30 seconds. The mixture was stirred overnight at this temperature. Next day 1 ml of 1M HCl was added and the reaction was stirred for 15 minutes. Proton NMR of the crude mixture was collected and then the product was purified by flash chromatography using ethyl acetate and hexanes (1:9).

TABLE 3

Catalyst screening for the allylboration of aldehydes:

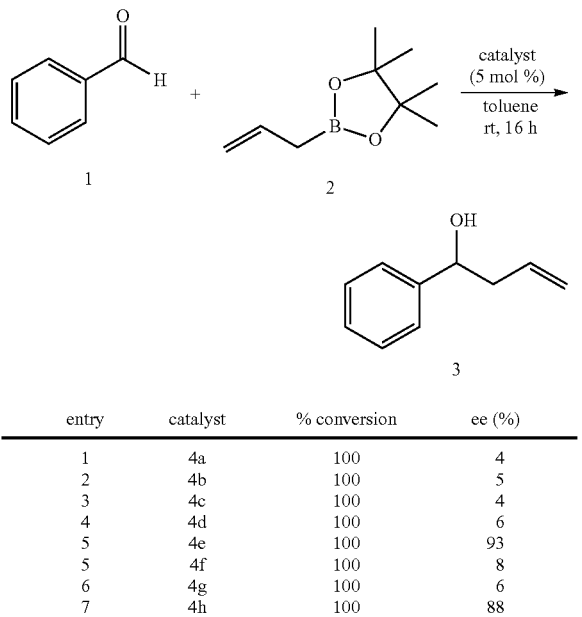

| entry | catalyst | % conversion | ee (%) |
|-------|----------|--------------|--------|
| 1 | 4a | 100 | 4 |
| 2 | 4b | 100 | 5 |
| 3 | 4c | 100 | 4 |
| 4 | 4d | 100 | 6 |
| 5 | 4e | 100 | 93 |
| 5 | 4f | 100 | 8 |
| 6 | 4g | 100 | 6 |
| 7 | 4h | 100 | 88 |

(R)-TRIP-PA was found to promote the crotylboration of benzaldehyde with high diastereo- and enantioselectivity, seen in Table 4. Use of (E)-crotylboronate 5a provided the anti isomer 6a exclusively with 96% ee at room temperature (entry 1) and >99% ee at 0° C. (entry 2) using the general reaction conditions. When (Z)-crotylboronate 5b was employed, the syn isomer 6b was obtained exclusively with 94% ee at −30° C.

TABLE 4

Asymmetric Crotylboration of Benzaldehyde[a]

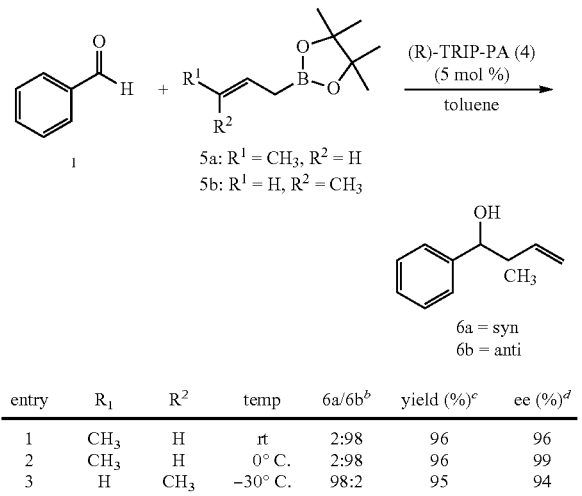

| entry | $R_1$ | $R^2$ | temp | 6a/6b[b] | yield (%)[c] | ee (%)[d] |
|-------|-------|-------|------|----------|--------------|-----------|
| 1 | CH$_3$ | H | rt | 2:98 | 96 | 96 |
| 2 | CH$_3$ | H | 0° C. | 2:98 | 96 | 99 |
| 3 | H | CH$_3$ | −30° C. | 98:2 | 95 | 94 |

[a]Reaction conditions: 1 (0.10 mmol), 2 (0.12 mmol), 5 mol % (R)-TRIP-PA.
[b]Determined by 1H NMR analysis.
[c]Isolated yield.
[d]Determined by chiral HPLC analysis.

Figure 3:
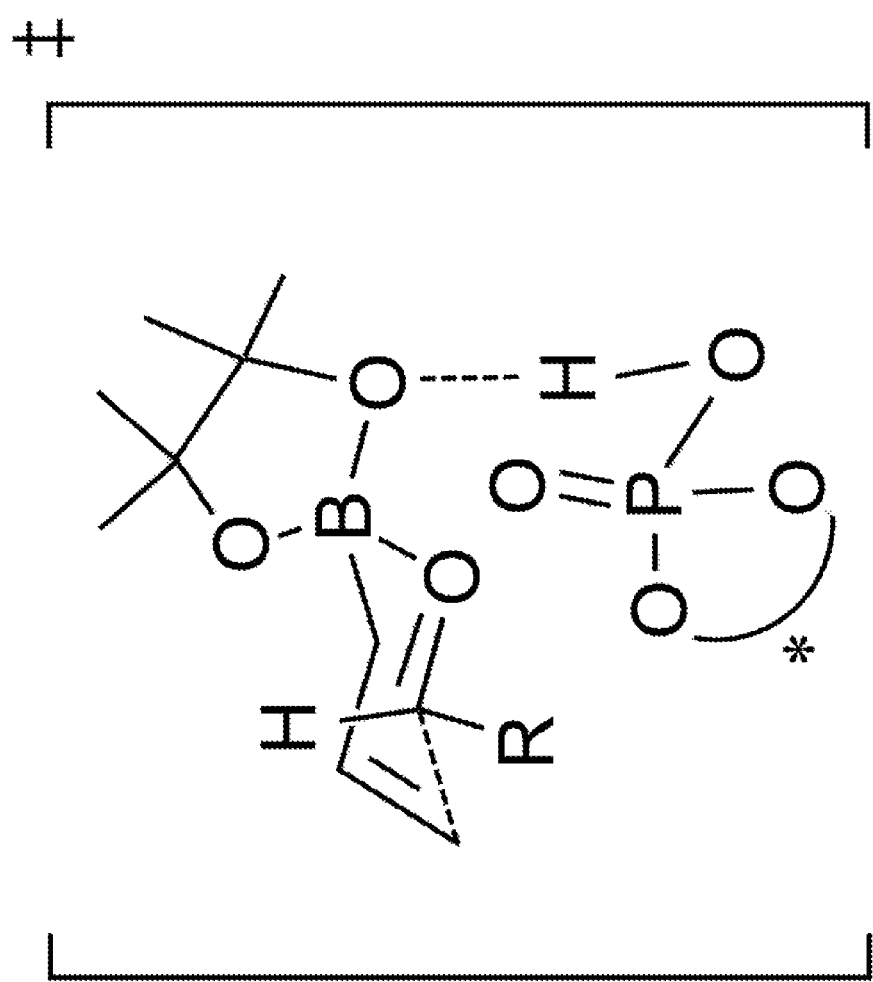
FIG. 3 is an image of the proposed transition-state assembly for chiral phosphoric acid-catalyzed allylation of aldehydes.

Although the reaction mechanism for this interesting activation has yet to be elucidated, the observed diastereoselectivity in the crotylation strongly suggests that the allylboration proceeds via a type-I mechanism involving a chair-like six-membered cyclic transition state, similar to previous uncatalyzed reactions involving allylboronates (Yang, J. E. *Six-Membered Transition States in Organic Synthesis*; Wiley: Hoboken, N.J., 2008; Chapter 3, pp 97-146. (b) Li, Y.; Houk, K. N. *J. Am. Chem. Soc.* 1989, 111, 1236). Recent work by Hall (Rauniyar, V.; Zhai, H.; Hall, D. G. *J. Am. Chem. Soc.* 2008, 130, 8481; Rauniyar, V.; Hall, D. G. *J. Org. Chem.* 2009, 74, 4236) and Schaus (Barnett, D. S.; Moquist, P. N.; Schaus, S. E. *Angew. Chem., Int. Ed.* 2009, 48, 8679) suggested that activation by protonation of the boronate oxygen could be involved. Similarly, Lewis acid-promoted boronate activation has also been invoked previously (Rauniyar, V.; Hall, D. G. *J. Am. Chem. Soc.* 2004, 126, 4518). Without being bound to a specific theory, the reaction likely occurs via protonation of the boronate oxygen by the chiral phosphoric acid catalyst, as seen in FIG. 3.

Allenylboration of Aldehydes

Figure 4:
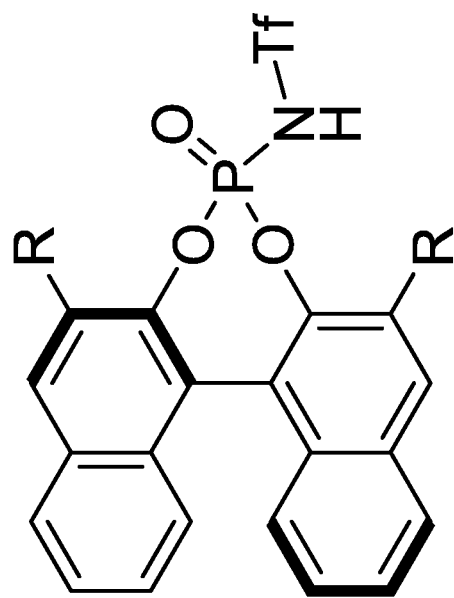
FIG. 4 is a structural diagram of catalysts evaluated for the propargylation of compounds in Tables 5 and 6.
Figure 4:
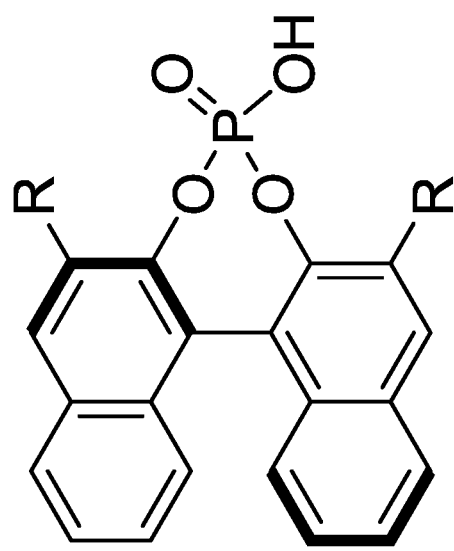

Based on the development of phosphoric acid catalyzed allylboration, allenylboration was used to synthesize nonracemic homopropargyl alcohols. Benzaldehyde was reacted with boronate 2, a relatively stable, non-toxic and commercially available reagent. The C—C bond formation proceeded smoothly in presence of various chiral acid-catalysts (Akiyama, T. *Chem. Rev.* 2007, 107, 5744; Doyle, A. G.; Jacobsen, E. N. *Chem. Rev.* 2007, 107, 5173; Terada, M. *Chem. Commun.* 2008, 4097) with complete regioselectivity, as seen in Table 5. PA5 (Hoffmann, S.; Seayad, A.; List, B. *Angew. Chem., Int. Ed.* 2005, 44, 7424), seen in FIG. 4, gave the best enantioselectivity along with toluene as the solvent. Superior selectivity was attained with higher catalyst loading in presence of 4 ÅMS (entry 13). Slight improvement in enantioselectivity was observed with the lowering of temperature to 0° C. (entry 14) and −20° C. (entry 15), albeit with longer reaction times.

TABLE 5

Catalyst screening and optimization of the catalytic propargylation of aldehydes[a]

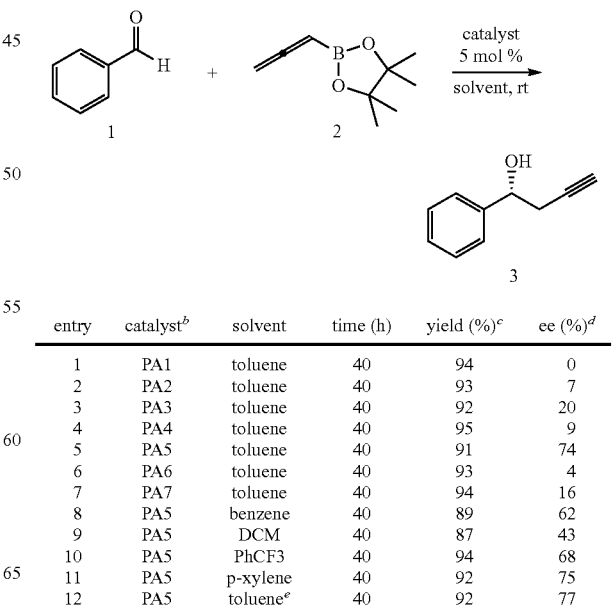

| entry | catalyst[b] | solvent | time (h) | yield (%)[c] | ee (%)[d] |
|-------|-------------|---------|----------|--------------|-----------|
| 1 | PA1 | toluene | 40 | 94 | 0 |
| 2 | PA2 | toluene | 40 | 93 | 7 |
| 3 | PA3 | toluene | 40 | 92 | 20 |
| 4 | PA4 | toluene | 40 | 95 | 9 |
| 5 | PA5 | toluene | 40 | 91 | 74 |
| 6 | PA6 | toluene | 40 | 93 | 4 |
| 7 | PA7 | toluene | 40 | 94 | 16 |
| 8 | PA5 | benzene | 40 | 89 | 62 |
| 9 | PA5 | DCM | 40 | 87 | 43 |
| 10 | PA5 | PhCF$_3$ | 40 | 94 | 68 |
| 11 | PA5 | p-xylene | 40 | 92 | 75 |
| 12 | PA5 | toluene[e] | 40 | 92 | 77 |

TABLE 5-continued

Catalyst screening and optimization of the catalytic propargylation of aldehydes[a]

| entry | catalyst[b] | solvent | time (h) | yield (%)[c] | ee (%)[d] |
|---|---|---|---|---|---|
| 13 | PA5 | toluene[e,f] | 24 | 93 | 87 |
| 14 | PA5 | toluene[e,f,g] | 64 | 96 | 90 |
| 15 | PA5 | toluene[e,f,h] | 72 | 94 | 91 |

[a]Reaction conditions: 1 (0.10 mmol), 2 (0.15 mmol), 5 mol % catalyst, unless otherwise specified.
[b]Catalysts were washed with 6M HCl after purification by column chromatography.
[c]Isolated yield.
[d]Determined by chiral HPLC analysis.
[e]Reaction conducted in presence of 4 Å MS.
[f]20 mol % chiral acid catalyst used.
[g]Reaction conducted at 0° C.
[h]Reaction conducted at −20° C.

Figure 5:
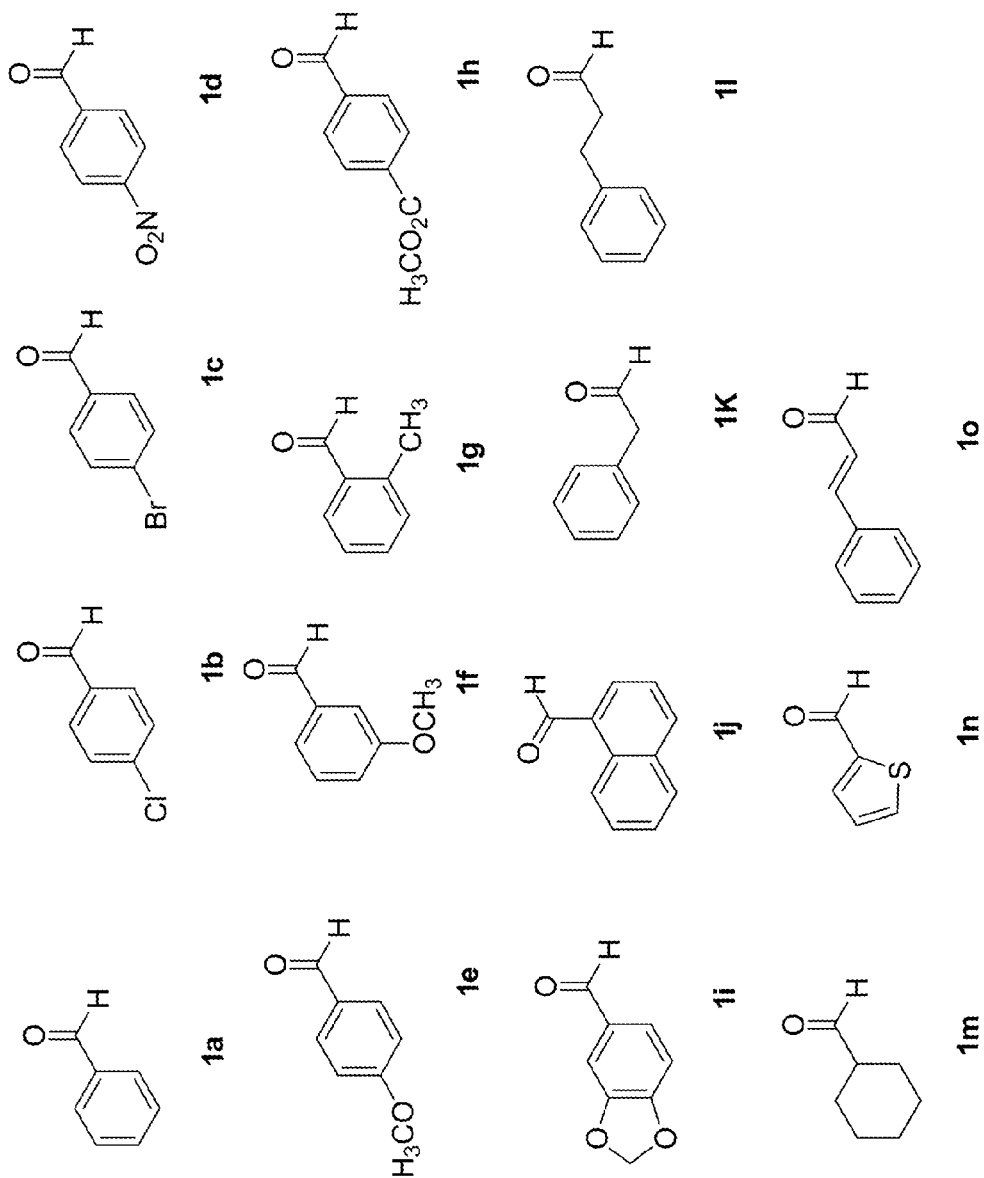
FIG. 5 is a structural diagram of starting reactants used in Table 6.

Having optimized the conditions, a range of various aldehydes were tested to study the scope and limitation of the developed methodology, as seen in Table 6. Though benzaldehyde showed >90% conversion in 48 hours, the reaction time was not further optimized and all the substrates were allowed to react for 96 hours to ensure complete conversion. The catalyst system showed tolerance to electron density effect (1b-1d for electron-withdrawing and 1e-1g electron-donating groups in comparison to 1a) giving excellent yields and selectivity (92-96% ee). An ester (1h, 91% ee), an ether (1i, 94% ee) tethered on the aromatic ring and a sterically hindered substrate (1j, 91% ee), seen in FIG. 5, were also well tolerated.

TABLE 6

Enantioselective propargylation of aldehydes[a]

94%, 91% ee, 3a

95%, 93% ee, 3b

93%, 93% ee, 3c

96%, 93% ee, 3d

87%, 92% ee, 3e

92%, 96% ee, 3f

91%, 92% ee, 3g

TABLE 6-continued

Enantioselective propargylation of aldehydes[a]

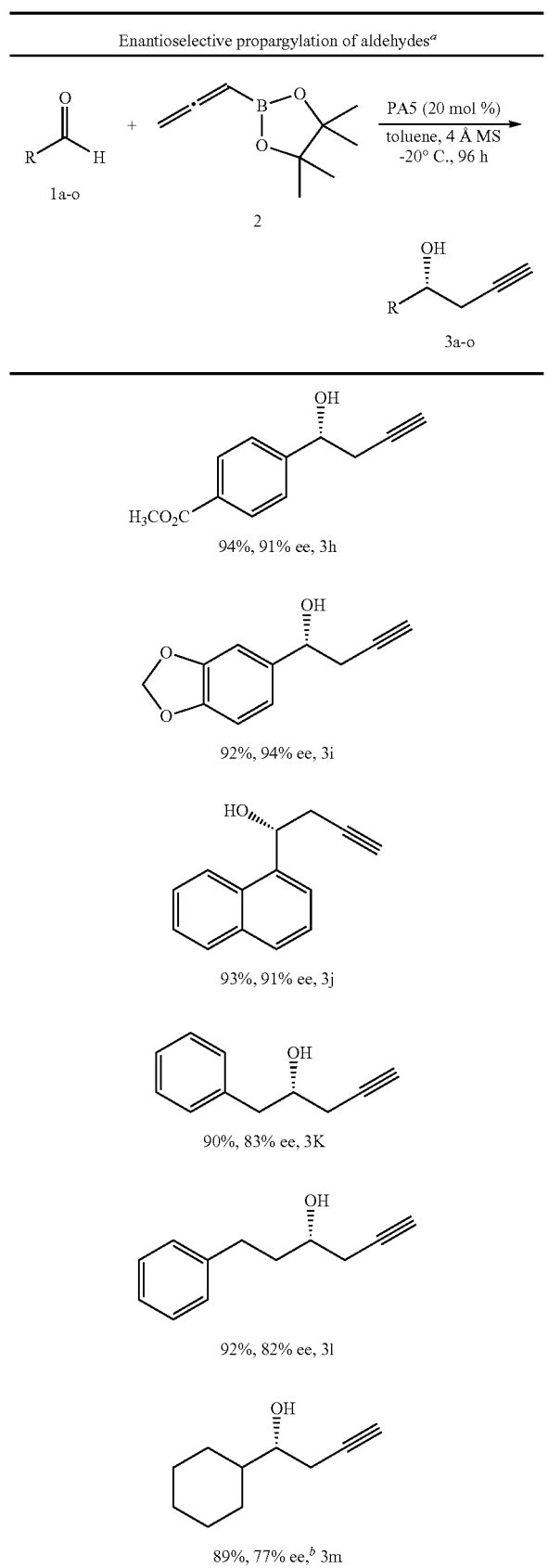

94%, 91% ee, 3h

92%, 94% ee, 3i

93%, 91% ee, 3j

90%, 83% ee, 3K

92%, 82% ee, 3l

89%, 77% ee,[b] 3m

TABLE 6-continued

Enantioselective propargylation of aldehydes[a]

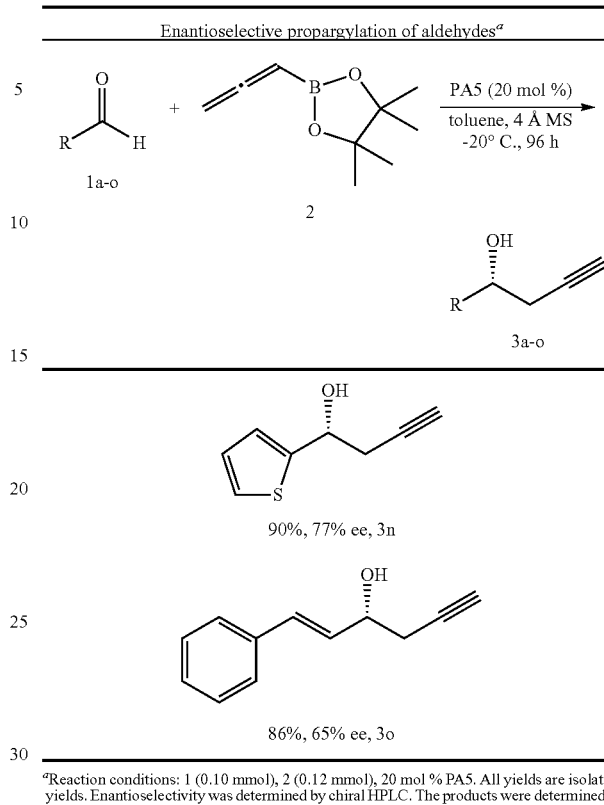

90%, 77% ee, 3n

86%, 65% ee, 3o

[a]Reaction conditions: 1 (0.10 mmol), 2 (0.12 mmol), 20 mol % PA5. All yields are isolated yields. Enantioselectivity was determined by chiral HPLC. The products were determined to be (R) by chiral HPLC analysis and optical rotation data in the literature.
[b]Enantioselectivity was determined by $^1$H NMR after conversion to the corresponding Mosher ester.

The procedure was also extended to aliphatic aldehydes with enantioselectivities of 77-83% ee, seen with compounds 1k-1m. The allenylboration proceeds via a six-membered cyclic transition state where the catalyst powers the reaction by protonation of the boronate oxygen.

A simple and highly efficient chiral phosphoric acid-catalyzed allylboration of aldehydes has been developed. The protocol provides a highly enantioselective method for the synthesis of homoallylic alcohols from simple starting materials. The reaction is simple and highly efficient with a broad scope in synthetic chemistry. The usefulness of this organocatalytic reaction is highlighted by the stability and commercial availability of the substrates and the catalyst.

EXAMPLES

The following reactions were carried out in flame-dried screw-cap test tubes and were allowed to proceed under a dry argon atmosphere with magnetic stirring. Toluene was purified by passing through a column of activated alumina under a dry argon atmosphere. A screw-cap reaction tube with a stir bar was evacuated, flame-dried, and back-filled with argon. Aldehydes were purchased from commercial sources and were distilled prior to use. TRIP catalyst was prepared from chiral BINOL according to the known literature procedure (Hoffmann, S.; Seayad, A.; List, B. *Angew. Chem., Int. Ed.* 2005, 44, 7424). To this tube was added the (R)-TRIP-PA catalyst 4 (5 mol %), freshly distilled aldehyde (0.1 mmol) and 1.5 ml of dry toluene. The reaction mixture was then cooled to −30° C. followed by the addition of allylboronic acid pinacol ester 2 (0.12 mmol), dropwise over 30 seconds. The mixture was stirred overnight at this temperature and then directly loaded on a silica gel column, the crude product was purified by flash chromatography using ethyl acetate and hexanes (1:9).

Thin layer chromatography was performed on Merck TLC plates (silica gel 60 $F_{254}$). Visualization was accomplished UV light (256 nm), with the combination of ceric ammonium molybdate as indicator. Flash column chromatography was performed with Merck silica gel (230-400 mesh). Enantiomeric excess (ee) was determined using a Varian Prostar HPLC with a 210 binary pump and a 335 diode array detector. Optical rotations were performed on a Rudolph Research Analytical Autopol IV polarimeter (λ 589) using a 700-μL cell with a path length of 1-dm. $^1$H NMR and $^{13}$C NMR were recorded on a Varian Inova-400 spectrometer with chemical shifts reported relative to tetramethylsilane (TMS). All the compounds were known compounds and were characterized by comparing their $^1$H NMR and $^{13}$C NMR values to the reported values.

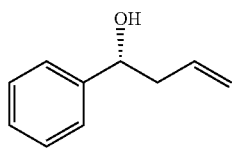

(R)-1-Phenyl-but-3-en-1-ol (3a)

Following the general procedure for the allylation of aldehydes, the title compound was obtained in 99% yield with spectral properties reported in literature (Wadamoto, M.; Ozasa, N.; Yanagigawa, A.; Yamamoto, H. *J. Org. Chem.* 2003, 68, 5593-5601). Enantiomeric excess was determined by HPLC with a chiralcel OD-H column (hexane/iPrOH=99/1, 0.7 mL/min), $t_{major}$=29.27 min, $t_{minor}$ 34.44 min; ee=98%. $[\alpha]^{24}_D$=+55.74 (c=0.98, CHCl$_3$). The reported value (Wadamoto, M.; Ozasa, N.; Yanagigawa, A.; Yamamoto, H. *J. Org. Chem.* 2003, 68, 5593-5601) for the R-enantiomer (95% ee) is $[\alpha]_D$=+56.5 (c=1.0, CHCl$_3$). $^1$H NMR (400 MHz, CDCl$_3$): δ 7.35-7.20 (m, 5H), 5.85-5.71 (m, 1H), 5.16-5.10 (m, 2H), 4.72 (dd, J=7.6, 5.6 Hz, 1H), 2.54-2.43 (m, 2H), 2.00 (br s, 1H).

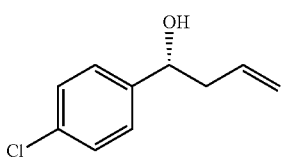

(R)-1-(4-Chloro-phenyl)-but-3-en-1-ol (3b)

Following the general procedure for the allylation of aldehydes, the title compound was obtained in 98% yield with spectral properties reported in literature (Wu. T. R.; Shen, L.; Chong, M. *Org. Lett.* 2004, 6, 2701-2704). Enantiomeric excess was determined by HPLC with a chiralcel AD-H column (hexane/iPrOH=99/1, 1.0 mL/min), $t_{major}$=26.59 min, $t_{minor}$=28.55 min; ee=99%. $[\alpha]^{24}_D$=+ 63.3 (c=1.14, CHCl$_3$). The reported value (Wu. T. R.; Shen, L.; Chong, M. *Org. Lett.* 2004, 6, 2701-2704) for the R-enantiomer (94% ee) is $[\alpha]_D$=+61.4 (c=1.17, CHCl$_3$). $^1$H NMR (400 MHz, CDCl$_3$): δ 2.04 (s, 1H), 2.39-2.52 (m, 2H), 4.66-4.73 (m, 1H), 4.96-5.20 (m, 2H), 5.69-5.83 (m, 1H), 7.18-7.35 (m, 4H).

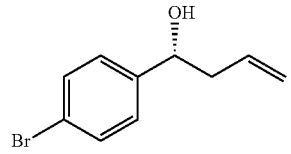

(R)-1-(4-Bromo-phenyl)-but-3-en-1-ol (3c)

Following the general procedure for the allylation of aldehydes, the title compound was obtained in 99% yield with spectral properties reported in literature (Wadamoto, M.; Ozasa, N.; Yanagigawa, A.; Yamamoto, H. *J. Org. Chem.* 2003, 68, 5593-560). Enantiomeric excess was determined by HPLC with a chiralcel OJ-H column (hexane/iPrOH=95/5, 0.4 mL/min), $t_{minor}$=25.61 min, $t_{major}$=28.16 min; ee=99%. $[\alpha]^{24}_D$=+ 25.82 (c=0.91, Benzene). The reported value (Wadamoto, M.; Ozasa, N.; Yanagigawa, A.; Yamamoto, H. *J. Org. Chem.* 2003, 68, 5593-5601) for the R-enantiomer (96% ee) is $[\alpha]_D$=+23.2 (c=1.17, Benzene). $^1$H NMR (400 MHz, CDCl$_3$): δ 7.47 (d, J=8.4 Hz, 2H), 7.23 (d, J=8.4 Hz, 2H), 5.83-5.71 (m, 1H), 5.18-5.13 (m, 2H), 4.69 (dd, J=7.6, 4.8 Hz, 1H), 2.52-2.39 (m, 2H), 2.06 (br s, 1H).

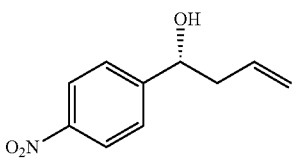

(R)-1-(4-Nitro-phenyl)-but-3-en-1-ol (3d)

Following the general procedure for the allylation of aldehydes, the title compound was obtained in 98% yield with spectral properties reported in literature (Burgos, C. H.; Canales, E.; Matos, K.; Soderquiest, J. A. *J. Am. Chem. Soc.* 2005, 127, 8044). Enantiomeric excess was determined by HPLC with a chiralcel AS-H column (hexane/iPrOH=97/3, 0.7 mL/min), $t_{major}$=52.09 min, $t_{minor}$=54.52 min; ee=98%. $[\alpha]^{24}_D$=+65.87 (c=1.07, CHCl$_3$). The reported value (Burgos, C. H.; Canales, E.; Matos, K.; Soderquiest, J. A. *J. Am. Chem. Soc.* 2005, 127, 8044) for the R-enantiomer (97% ee) is $[\alpha]_D$=+64.2 (c=0.8, CHCl$_3$). 1H NMR (400 MHz, CDCl$_3$): δ 8.23 (d, J=8.8 Hz, 2H), 7.56 (d, J=8.8 Hz, 2H), 5.86-5.72 (m, 1H), 5.24-5.17 (m, 2H), 4.89 (m, 1H), 2.61-2.55 (m, 1H), 2.52-2.44 (m, 1H) 2.31 (br s, 1H).

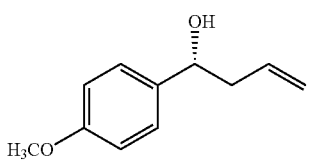

(R)-1-(4-Methoxy-phenyl)-but-3-en-1-ol (3e)

Following the general procedure for the allylation of aldehydes, the title compound was obtained in 95% yield with spectral properties reported in literature (Wu. T. R.; Shen, L.; Chong, M. *Org. Lett.* 2004, 6, 2701-2704). Enantiomeric excess was determined by HPLC with a chiralcel OD-H column (hexane/iPrOH=98/2, 1.0 mL/min), $t_{major}$=18.64 min, $t_{minor}$=22.87 min; ee=98%. $[\alpha]^{24}_D$=+30.84 (c=1.01, Benzene). The reported value (Wu. T. R.; Shen, L.; Chong, M. *Org. Lett.* 2004, 6, 2701-2704) for the R-enantiomer (95% ee) is $[\alpha]_D$=+30.5 (c=1.0, Benzene). $^1$H NMR (400 MHz, CDCl3): δ 7.25 (d, J=8.0 Hz, 2H), 6.86 (d, J=8.0 Hz, 2H), 5.83-5.72 (m, 1H), 5.16-5.09 (m, 2H), 4.69 (m, 1H), 3.78 (s, 3H), 2.50 (m, 2H), 1.95 (br s, 1H).

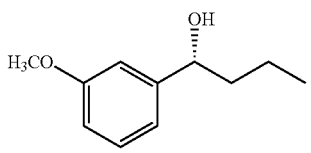

(R)-1-(3-Methoxy-phenyl)-but-3-en-1-ol (3f)

Following the general procedure for the allylation of aldehydes, the title compound was obtained in 96% yield with spectral properties reported in literature (Zheng, Y.; Zhou, J.; Loh. T. *Org. Lett.* 1999, 11, 1855-1857). Enantiomeric excess was determined by HPLC with a chiralcel OJ-H column (hexane/iPrOH=98/2, 0.8 mL/min), tminor=28.63 min, tmajor=30.17 min; ee=97%. $[\alpha]^{24}_D$=+53.81 (c=0.89, Benzene). The reported value (Zheng, Y.; Zhou, J.; Loh. T. *Org. Lett.* 1999, 11, 1855-1857) for the R-enantiomer (73% ee) is $[\alpha]_D$=+41.0 (c=2.22, Benzene). $^1$H NMR (400 MHz, CDCl3): δ 7.27-7.22 (m, 1H) 6.94-6.89 (m, 2H), 6.82-6.78 (m, 1H), 5.85-5.47 (m, 1H), 5.19-5.10 (m, 2H), 4.67-4.72 (m, 1H), 3.80 (s, 3H), 2.56-2.42 (m, 2H), 1.95 (br s, 1H).

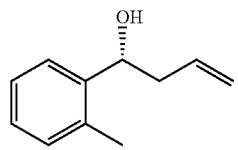

(R)-1-o-Tolyl-but-3-en-1-ol (3g)

Following the general procedure for the allylation of aldehydes, the title compound was obtained in 97% yield with spectral properties reported in literature (Wadamoto, M.; Ozasa, N.; Yanagigawa, A.; Yamamoto, H. *J. Org. Chem.* 2003, 68, 5593-5601). Enantiomeric excess was determined by HPLC with a chiralcel AD-H column (hexane/iPrOH=95/5, 0.5 mL/min), $t_{major}$=13.89 min, $t_{minor}$=16.32 min; ee=93%. $[\alpha]^{24}_D$=+68.8 (c=1.11, Benzene). The reported value (Wadamoto, M.; Ozasa, N.; Yanagigawa, A.; Yamamoto, H. *J. Org. Chem.* 2003, 68, 5593-5601) for the R-enantiomer (97% ee) is $[\alpha]_D$=+75.5 (c=1.0, Benzene). $^1$H NMR (400 MHz, CDCl$_3$): δ 7.49 (d, J=7.8 Hz, 1H), 7.28-7.12 (m, 3H) 5.22-5.14 (m, 2H), 4.97 (dd, J=8.0, 4.8 Hz, 1H), 2.54-2.40 (m, 2H), 2.35 (s, 3H), 2.02 (br s, 1H).

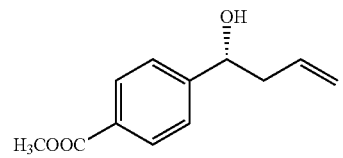

(R)-Methyl 4-(1-hydroxybut-3enyl)benzoate (3h)

Following the general procedure for the allylation of aldehydes, the title compound was obtained in 96% yield with spectral properties reported in literature (Kim, I. S.; Ngai, M.; Krische, M. J. *J. Am. Chem. Soc.* 2008, 130, 14891). Enantiomeric excess was determined by HPLC with a chiralcel AD-H column (hexane/iPrOH=95/5, 0.6 mL/min), $t_{major}$=23.67 min, $t_{minor}$=26.84 min; ee=96%. $[\alpha]^{24}_D$=27.84 (c=1.31, Benzene). $^1$H NMR (400 MHz, CDCl3): δ 8.00 (d, J=8.0 Hz, 2H), 7.42 (d, J=8.0 Hz, 2H), 5.83-5.72 (m, 1H), 5.17-5.12 (m, 2H), 4.79 (dd, J=8.0, 4.8 Hz, 1H), 3.90 (s, 3H), 2.56-2.41 (m, 2H), 2.24 (br s, 1H).

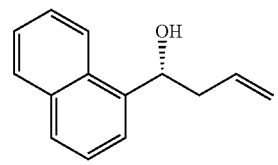

(R)-1-Naphthalen-1-yl-but-3-en-1-ol (3l)

Following the general procedure for the allylation of aldehydes, the title compound was obtained in 93% yield with spectral properties reported in literature (Wadamoto, M.; Ozasa, N.; Yanagigawa, A.; Yamamoto, H. *J. Org. Chem.* 2003, 68, 5593-5601). Enantiomeric excess was determined by HPLC with a chiralcel OD-H column (hexane/iPrOH=90/10, 0.5 mL/min), $t_{minor}$=16.44 min, $t_{major}$=26.73 min; ee=98%. $[\alpha]^{24}_D$=+98.63 (c=1.06, Benzene). The reported value (Wadamoto, M.; Ozasa, N.; Yanagigawa, A.; Yamamoto, H. *J. Org. Chem.* 2003, 68, 5593-5601) for the R-enantiomer (92% ee) is $[\alpha]_D$=+97.3 (c=1.0, Benzene). $^1$H NMR (400 MHz, CDCl$_3$): δ 8.09 (d, J=8.2 Hz, 1H), 7.88 (d, J=7.8 Hz, 1H), 7.79 (d, J=8.2 Hz, 1H), 7.68 (d, J=7.1 Hz, 1H), 7.55-7.45 (m, 3H), 6.00-5.87 (m, 1H), 5.58-5.52 (m, 1H), 5.28-5.16 (m, 2H), 2.80-2.56 (m, 2H), 2.14 (br s, 1H).

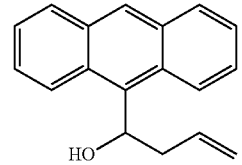 [SMILES: C=CCC(O)c1c2ccccc2cc2ccccc12]

(R)-1(anthrcen-9-yl)but-3-en-1-ol (3j)

Following the general procedure for the allylation of aldehydes, the title compound was obtained in 93% yield with spectral properties reported in literature (Bold, G.; Duthaler, R. D.; Riediker, M. *Angew. Chem.* 1989, 101, 491-493). Enantiomeric excess was determined by HPLC with a chiralcel AD-H column (hexane/iPrOH=95/5, 1.0 mL/min), $t_{major}$=17.60 min, $t_{minor}$=21.29 min; ee=91%. $[\alpha]^{24}_D$=+17.38 (c=1.85, CHCl$_3$). $^1$H NMR (400 MHz, CDCl$_3$): δ 8.72-8.60 (m, 2H), 8.39 (s, 1H), 8.02-7.97 (m, 2H), 7.51-7.42 (m, 4H), 6.29 (dd, J=6.3 Hz, 1H), 6.01-5.90 (m, 1H), 5.29-5.10 (m, 2H), 3.24-3.15 (m, 1H), 2.89-2.81 (m, 1H), 2.25 (br s, 1H).

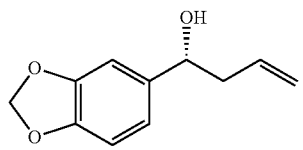

(R)-1-(Benzo[d][1,3]dioxol-5-yl)but-3-en-1-ol (3k)

Following the general procedure for the allylation of aldehydes, the title compound was obtained in 98% yield with spectral properties reported in literature (Kim, I. S.; Ngai, M.; Krische, M. J. *J. Am. Chem. Soc.* 2008, 130, 14891). Enantiomeric excess was determined by HPLC with a chiralcel OD-H column (hexane/iPrOH=98/2, 1.0 mL/min), $t_{major}$=22.37 min, $t_{minor}$=27.64 min; ee=98%. $[\alpha]^{24}_D$=+35.53 (c=0.95, CHCl$_3$). $^1$H NMR (400 MHz, CDCl$_3$): δ 6.86 (m, 1H), 6.81-6.75 (m, 2H), 5.95 (s, 2H), 5.84-5.72 (m, 1H), 5.18-5.11 (m, 2H), 4.65 (t, J=6.8 Hz, 1H), 2.46 (t, J=6.4 Hz, 2H), 1.96 (br s, 1H).

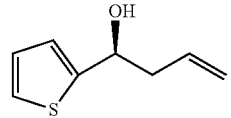

(S)-1-Thiophen-2-yl-but-3-en-1-ol (3l)

Following the general procedure for the allylation of aldehydes, the title compound was obtained in 91% yield with spectral properties reported in literature (Singh, S.; Kumar, S.; Chimni, S. S. *Tetrahedron Asym.* 2002, 13, 2679-2687). Enantiomeric excess was determined by HPLC with a chiralcel OJ-H column (hexane/iPrOH=93/7, 0.5 mL/min), $t_{minor}$=21.37 min, $t_{major}$=24.59 min; ee=96%. $[\alpha]^{24}_D$=-12.33 (c=1.07, CHCl$_3$). The reported value (Xia, G; Yamamoto, H. *J. Am. Chem. Soc.* 2006, 128, 2554-2555) for the R-enantiomer (95% ee) is $[\alpha]_D$=+9.7 (c=1.0, EtOH). $^1$H NMR (400 MHz, CDCl$_3$): δ 7.27-7.24 (m, 1H), 6.98-6.94 (m, 2H), 5.87-5.76 (m, 1H), 5.20-5.14 (m, 2H), 4.96-5.00 (m, 1H), 2.63-2.59 (m, 2H), 2.10-2.11 (m, 1H).

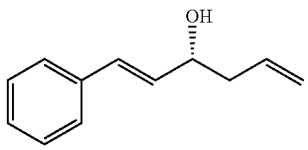

(R),(E)-1-Phenyl-hexa-1,5-dien-3-ol (3m)

Following the general procedure for the allylation of aldehydes, the title compound was obtained in 94% yield with spectral properties reported in literature (Wadamoto, M.; Ozasa, N.; Yanagigawa, A.; Yamamoto, H. *J. Org. Chem.* 2003, 68, 5593-5601). Enantiomeric excess was determined by HPLC with a chiralcel AS-H column (hexane/iPrOH=95/5, 1.0 mL/min), $t_{major}$=8.00 min, $t_{minor}$=9.04 min; ee=96%. $[\alpha]^{24}_D$=-9.76 (c=1.12, Et$_2$O). The reported value (Wadamoto, M.; Ozasa, N.; Yanagigawa, A.; Yamamoto, H. *J. Org. Chem.* 2003, 68, 5593-5601) for the R-enantiomer (97% ee) is $[\alpha]_D$=-12.3 (c=1.0, Et$_2$O). $^1$H NMR (400 MHz, CDCl$_3$): δ 7.39-7.21 (m, 5H), 6.60 (d, J=16.0 Hz, 1H), 6.23 (dd, J=16.0, 6.4 Hz, 1H), 5.90-5.80 (m, 1H), 5.20-5.14 (m, 2H), 4.35 (ddd, J=6.8, 6.0, 6.0 Hz, 1H), 2.45-2.33 (m, 2H), 1.80 (br s, 1H).

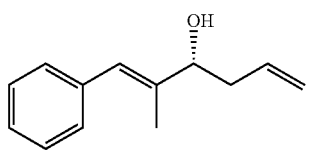

(R),(E)-2-Methyl-1-phenyl-hexa-1,5-dien-3-ol (3n)

Following the general procedure for the allylation of aldehydes, the title compound was obtained in 93% yield with spectral properties reported in literature (Malkov, A.; Dufkova, L.; Farrugia, L.; Kocovsky, P. *Angew. Chem. Int. Ed.* 2003, 42, 3674-3677). Enantiomeric excess was determined by HPLC with a chiralcel OD-H column (hexane/iPrOH=97/3, 1.0 mL/min), $t_{major}$=10.85 min, $t_{minor}$=12.64 min; ee=93%. $[\alpha]^{24}_D$=+2.37 (c=0.79, CHCl$_3$). The reported value 10 for the R-enantiomer (50% ee) is $[\alpha]_D$=+1.1 (c=1.15, CHCl$_3$). $^1$H NMR (400 MHz, CDCl$_3$): δ 1.82-1.84 (m, 1H), 1.87-1.88 (m, 3H), 2.34-2.48 (m, 2H), 4.17-4.25 (m, 1H), 5.11-5.21 (m, 2H), 5.77-5.88 (m, 1H), 6.52 (s, 1H), 7.18-7.35 (m, 5H).

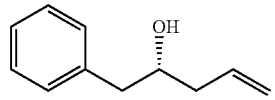

(R)-1-Phenylpent-4-en-2-ol (3o)

Following the general procedure for the allylation of aldehydes, the title compound was obtained in 98% yield with spectral properties reported in literature (Rauniyar, V.; Zhai, H.; Hall, D. G. *J. Am. Chem. Soc.* 2008, 130, 8481). Enantiomeric excess was determined by HPLC with a chiralcel OD-H column (hexane/iPrOH=97/3, 0.5 mL/min), $t_{minor}$=15.51 min, $t_{major}$=19.65 min; ee=90%. $[\alpha]^{24}_D$=-12.20 (c=1.01). The reported value (Rauniyar, V.; Zhai, H.; Hall, D. G. *J. Am. Chem. Soc.* 2008, 130, 8481) for the R-enantiomer (97% ee) is $[\alpha]_D$=-14.24 (c=0.65, CHCl$_3$). $^1$H NMR (400 MHz, CDCl$_3$): δ 7.35-7.20 (m, 5H), 5.94-5.80 (m, 1H), 5.20-5.12 (m, 2H), 3.93-3.84 (m, 1H), 2.86-2.70 (m, 2H), 2.38-2.18 (m, 2H), 1.7 (br s, 1H).

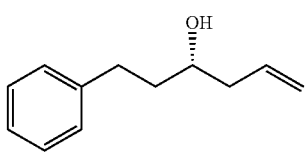

(S)-1-Phenylpent-4-en-2-ol (3p)

Following the general procedure for the allylation of aldehydes, the title compound was obtained in 96% yield with spectral properties reported in literature (Wadamoto, M.; Ozasa, N.; Yanagigawa, A.; Yamamoto, H. *J. Org. Chem.* 2003, 68, 5593-5601). Enantiomeric excess was determined by HPLC with a chiralcel OD-H column (hexane/iPrOH=95/5, 1.0 mL/min), $t_{major}$=8.76 min, $t_{minor}$=13.29 min; ee=87%. $[\alpha]^{24}_D$=−25.4 (c=0.97, Benzene). The reported value (Wadamoto, M.; Ozasa, N.; Yanagigawa, A.; Yamamoto, H. *J. Org. Chem.* 2003, 68, 5593-5601) for the S-enantiomer (86% ee) is $[\alpha]_D$=−26.4 (c=1.0, Benzene). $^1$H NMR (400 MHz, CDCl$_3$): δ 1.76-1.84 (m, 2H), 2.14-2.37 (m, 2H), 2.64-2.86 (m, 2H), 3.62-3.72 (m, 1H), 5.08-5.19 (m, 2H), 5.72-5.98 (m, 1H), 7.13-7.32 (m, 5H).

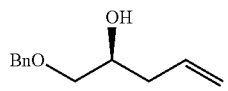

(S)-1-Benzyloxy-pent-4-en-2-ol (3q)

Following the general procedure for the allylation of aldehydes, the title compound was obtained in 92% yield with spectral properties reported in literature (Lee, J.; Miller, J. J.; Hamilton, S. S.; Sigman, S. S. *Org. Lett.* 2005, 7, 1837-1839). Enantiomeric excess was determined by HPLC with a chiralcel AS-H column (hexane/iPrOH=97/3, 0.5 mL/min), $t_{minor}$=20.91 min, $t_{major}$=25.09 min; ee=79%. $[\alpha]^{24}_D$=−1.26 (c=1.27, CHCl$_3$). The reported value (Lee, J.; Miller, J. J.; Hamilton, S. S.; Sigman, S. S. *Org. Lett.* 2005, 7, 1837-1839) for the R-enantiomer (53% ee) is $[\alpha]_D$=+0.9 (c=2.5, CHCl$_3$). $^1$H NMR (400 MHz, CDCl$_3$): δ 7.37-7.24 (m, 5H), 5.87-5.75 (m, 1H), 5.13-5.06 (m, 2H), 4.54 (s, 2H), 3.92-3.84 (m, 1H), 3.50 (dd, J=9.2, 3.6 Hz, 1H), 3.36 (dd, J=9.6, 7.6 Hz, 1H), 2.35 (br s, 1H), 2.25 (t, J=6.8 Hz, 2H).

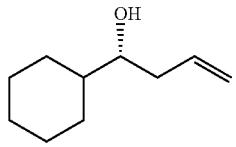

(R)-1-Cyclohexyl-but-3-en-1-ol (3r)

Following the general procedure for the allylation of aldehydes, the title compound was obtained in 98% yield with spectral properties reported in literature (Wadamoto, M.; Ozasa, N.; Yanagigawa, A.; Yamamoto, H. *J. Org. Chem.* 2003, 68, 5593-5601). Enantiomeric excess was determined by formation of 3,5 dinitrobenzoate ester of the title compound followed by HLPC with a chiralcel OD-H column (hexane/iPrOH=95/5, 1.0 mL/min), tmajor=10.97 min, tminor=11.76 min; ee=73%. $[\alpha]^{24}_D$=+ 5.24 (c=1.0, EtOH). The reported value (Wadamoto, M.; Ozasa, N.; Yanagigawa, A.; Yamamoto, H. *J. Org. Chem.* 2003, 68, 5593-5601) for the R-enantiomer (93% ee) is $[\alpha]_D$=+13.7 (c=1.0, EtOH). $^1$H NMR (400 MHz, CDCl$_3$): δ 0.91-1.32 (m, 4H), 1.55-1.87 (m, 7H), 2.16-2.08 (m, 1H), 2.30-2.37 (m, 1H), 3.42-3.35 (m, 1H), 5.16-5.10 (m, 2H), 5.90-5.78 (m, 1H).

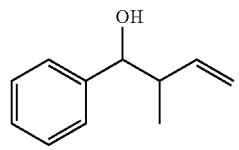

1-Methyl-1-phenyl-but-3-en-1-ol (6a)

Following the general procedure for the crotylboration of aldehydes, the syn product was obtained when cis-crotylboronic acid pinacol ester was used at −30° C., in 95% yield with spectral properties reported in literature (Wadamoto, M.; Ozasa, N.; Yanagigawa, A.; Yamamoto, H. *J. Org. Chem.* 2003, 68, 5593-5601). Enantiomeric excess was determined by HPLC with a chiralcel OD-H column (hexane/iPrOH=95/5, 1.0 mL/min), $t_{minor}$=7.17 min, $t_{major}$=8.32 min; ee=93%. $[\alpha]^{24}_D$=+19.27 (c=2.27, CHCl3). The absolute configuration of the syn isomer was found to be (1R,2S) by comparing with the literature (Wadamoto, M.; Ozasa, N.; Yanagigawa, A.; Yamamoto, H. *J. Org. Chem.* 2003, 68, 5593-5601). $^1$H NMR (400 MHz, CDCl$_3$): δ 0.99 (d, J=6.8 Hz, 3H), 1.94-1.96 (m, 1H), 2.52-2.62 (m, 1H), 4.60 (dd, J=5.5 Hz, 1H), 5.01-5.07 (m, 2H), 5.70-5.80 (m, 1H), 7.22-7.35 (m, 5H).

Crude proton NMR spectrum (after quench with 1M HCl) showing the syn-product when (Z)-crotyl boronate 5b was used.

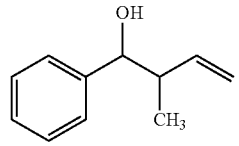

1-Methyl-1-phenyl-but-3-en-1-ol (6b)

Following the general procedure for the crotylboration of aldehydes, the anti product was obtained when trans-crotylboronic acid pinacol ester was used at −0° C., in 96% yield with spectral properties reported in literature (Wadamoto, M.; Ozasa, N.; Yanagigawa, A.; Yamamoto, H. *J. Org. Chem.* 2003, 68, 5593-5601). Enantiomeric excess was determined by HPLC with a chiralcel AD-H column (hexane/iPrOH=98/2, 1.0 mL/min)) $t_{minor}$=12.73 min, $t_{major}$=13.77 min; ee=99%. $[\alpha]^{24}_D$=98.97 (c=2.27, CHCl3). The absolute configuration of the anti isomer was found to be (1R,2R) by comparing with the literature (Wadamoto, M.; Ozasa, N.; Yanagigawa, A.; Yamamoto, H. *J. Org. Chem.* 2003, 68, 5593-5601). $^1$H NMR (400 MHz, CDCl$_3$): δ 0.88 (d, J=6.8 Hz, 3H), 2.13 (br s, 1H), 2.41-2.60 (m, 1H), 4.36 (d, J=7.8 Hz, 1H), 5.12-5.26 (m, 2H), 5.66-5.86 (m, 1H), 7.20-7.37 (m, 5H).

Crude proton NMR spectrum (after quench with 1M HCl) showing the anti-product when (E)-crotyl boronate 5b was used.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of a method for preparing homoallyl alcohols, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A method of synthesizing homoallyl or homopropargyl alcohols, comprising the steps of:
    obtaining an aldehyde, where the aldehyde does not possess a protecting group;
    obtaining an allylboronate or allenylboronate, where the allylboronate or allenylboronate does not possess a protecting group;
    lowering the temperature of the aldehyde and the allylboronate or allenylboronate to between about 0° C. and about −30° C.;
    reacting the aldehyde with the allylboronate or allenylborate in the presence of a chiral acid catalyst, wherein the chiral acid catalyst has the formula

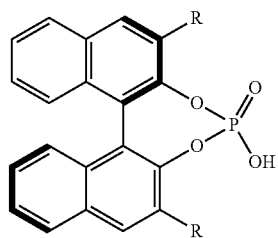

(I)

where R=SiPh3, 4-(b-Nath)-Ph, 9-anthryl, 4-(a-Naph)-Ph, (2,4,6-i-Pr)-Ph, or (2,5-CF3)-Ph; and
wherein the reaction forms a homoallyl alcohol.

2. The method of claim 1, wherein the aldehyde is selected from the group consisting of aromatic aldehydes, heteroaryl aldehydes, α,β-unsaturated aldehydes and aliphatic aldehydes.

3. The method of claim 1, further comprising reacting the aldehyde and allylboronate in a solvent, wherein the solvent is toluene, m-xylene, benzene, methylene chloride, ether, or DCM.

4. The method of claim 3, wherein the solvent is toluene.

5. The method of claim 1, wherein the chiral acid catalyst is (R)-3,3'-Bis(2,4,6-triisopropylphenyl)-1,1'-binaphthyl-2,2'-diyl hydrogenphosphate.

6. The method of claim 1, wherein the temperature of the reactants is 0° C. or −30° C.

7. The method of claim 1, wherein the chiral acid catalyst is at a catalyst loading amount of between about 5 mol %, and about 1 mol %.

8. The method of claim 7, wherein the chiral acid catalyst is at a catalyst loading amount of 5 mol %, 2.5 mol %, or 1 mol %.

9. The method of claim 1, further comprising adding a 4 Å molecular sieve and at a catalyst loading amount of 20 mol %.

10. The method of claim 9, further comprising lowering the temperature of the reactants to between about 0° C. and about −20° C.

11. The method of claim 9, wherein the temperature of the reactants is 0° C. or −20° C.

12. The method of claim 2, wherein the aldehydes are heteroaryl, α,β-unsaturated, or aliphatic.

13. The method of claim 7, wherein the chiral acid catalyst is at a catalyst loading amount of 2.5 mol % or 1 mol %.

* * * * *